United States Patent
Grenon et al.

(10) Patent No.: US 6,783,497 B2
(45) Date of Patent: Aug. 31, 2004

(54) TWO-DIMENSIONAL ULTRASONIC ARRAY WITH ASYMMETRIC APERTURES

(75) Inventors: Stephen Michael Grenon, Hillsborough, NC (US); Ronald E. Hileman, Durham, NC (US)

(73) Assignee: Volumetrics Medical Imaging, Inc., Hillsborough, NC (US)

( * ) Notice: Subject to any disclaimer, the term of this patent is extended or adjusted under 35 U.S.C. 154(b) by 0 days.

(21) Appl. No.: 10/154,149

(22) Filed: May 23, 2002

(65) Prior Publication Data

US 2003/0220554 A1 Nov. 27, 2003

(51) Int. Cl.[7] .................................................. A61B 8/14
(52) U.S. Cl. .................. 600/459; 600/437; 600/462; 310/320; 310/321; 310/322
(58) Field of Search ................................ 600/437–472; 367/87

(56) References Cited

U.S. PATENT DOCUMENTS

| | | | | |
|---|---|---|---|---|
| 4,023,175 A | * | 5/1977 | Brown et al. ................ 342/179 |
| 4,219,846 A | * | 8/1980 | Auphan ....................... 348/163 |
| 4,241,611 A | * | 12/1980 | Specht et al. ................. 73/626 |
| 4,398,116 A | * | 8/1983 | Lewis .......................... 310/334 |
| 4,523,471 A | * | 6/1985 | Lee ............................... 73/626 |
| 4,534,221 A | * | 8/1985 | Fife et al. ...................... 73/626 |
| 4,537,074 A | * | 8/1985 | Dietz ........................... 73/625 |
| 4,596,145 A | | 6/1986 | Smith et al. |
| 4,598,716 A | | 7/1986 | Hileman |
| 4,641,660 A | * | 2/1987 | Bele ............................. 600/459 |
| 4,694,434 A | | 9/1987 | von Ramm et al. |
| 5,109,857 A | | 5/1992 | Roundhill et al. |
| 5,191,890 A | | 3/1993 | Hileman |
| 5,278,757 A | * | 1/1994 | Hoctor et al. ............... 600/459 |
| 5,349,262 A | | 9/1994 | Grenon et al. |
| 5,419,329 A | | 5/1995 | Smith et al. |

(List continued on next page.)

OTHER PUBLICATIONS

T.S. Sumanaweera, J. Schwartz and D. Napolitano, "A spiral 2D phased array for imaging", in *Proc. IEEE Ultrason. Symp.*, vol 2, (Lake Tako, NV), pp. 1271–1274 Oct. 1999.

(List continued on next page.)

*Primary Examiner*—Francis J. Jaworski
*Assistant Examiner*—William Jung
(74) *Attorney, Agent, or Firm*—Kevin E. Flynn; Daniels Daniels & Verdonik,, P.A.

(57) ABSTRACT

A sparse array that uses a small fraction of a fully populated array but yields a radiation pattern that is suitable for high quality medical imaging. The sparse array consists of two or more separate zones for transmitting and receiving as opposed to the overlapping arrays of the prior art. More specifically, a preferred embodiment sets forth an inner array of transmit elements with a narrow effective aperture and a separate non-overlapping outer array of receive elements with a wide effective aperture. The combination of asymmetric apertures is particularly useful for parallel processing applications. This abstract is provided as a tool for those searching for patents, and not as a limitation on the scope of the claims.

23 Claims, 19 Drawing Sheets

U.S. PATENT DOCUMENTS

| | | | |
|---|---|---|---|
| 5,492,121 A | * | 2/1996 | Lu .............................. 600/459 |
| 5,537,367 A | * | 7/1996 | Lockwood et al. ........... 367/87 |
| 5,546,807 A | | 8/1996 | Oxaal et al. |
| 5,677,491 A | * | 10/1997 | Ishrak et al. .................. 73/641 |
| 5,740,128 A | | 4/1998 | Hossack et al. |
| 5,744,898 A | | 4/1998 | Smith et al. |
| 5,911,692 A | * | 6/1999 | Hussain et al. ............. 600/447 |
| 5,924,986 A | * | 7/1999 | Chandler et al. ........... 600/407 |
| 6,029,518 A | * | 2/2000 | Oeftering ................... 73/570.5 |
| 6,066,095 A | | 5/2000 | Morsy et al. |
| 6,066,096 A | * | 5/2000 | Smith et al. ................. 600/439 |
| 6,126,602 A | | 10/2000 | Savord et al. |
| 6,135,971 A | | 10/2000 | Hutchinson et al. |
| 6,159,153 A | | 12/2000 | Dubberstein et al. |
| 6,238,348 B1 | | 5/2001 | Crowley et al. |
| 6,241,675 B1 | | 6/2001 | Smith et al. |
| 6,276,211 B1 | | 8/2001 | Smith |
| 6,381,197 B1 | | 4/2002 | Savord et al. |
| 6,419,633 B1 | * | 7/2002 | Robinson et al. ........... 600/443 |
| 6,500,123 B1 | | 12/2002 | Holloway et al. |
| 6,544,178 B1 | | 4/2003 | Grenon et al. |

OTHER PUBLICATIONS

Lockwood et al., *Optimizing the Radiation Pattern of Sparse Periodic Two–Dimensional Arrays*, IEEE, Transactions on Ultrasonics, Ferroelectrics, and Frequency Control, vol. 43, No. 1, pp. 15–19, (Jan. 1996).

Emery et al., *Improved Signal–to–Noise Ratio in Hybrid 2–D Arrays: Experimental Confirmation*, Ultrasonic Imaging, vol. 19, pp. 93–111, (1997).

Austeng et al., *1D and 2D Algorithmically Optimized Sparse Arrays*, 1999 IEEE Ultrasonics Symposium, pp. 1683–1686, (1997).

Hussain et al., *Synthesis of Two–Dimensional Wideband Ultrasound Transducer Sparse Arrays*, SPIE Conference on Ultrasonic Transducer Engineering, San Diego, California, vol. 3664, pp. 167–179 (1999).

Holm, Sverre, *Bessel and Conical Beams and Approximation with Annular Arrays*, Department of Informatics, University of Oslo, Norway, pp. 1–2 and 2 drawings (undated).

Lu et al., *A Study of Two–Dimensional Array Transducers for Limited Diffraction Beams*, IEEE, Transactions on Ultrasonics, Ferroelectrics, and Frequency Control, vol. 41, No. 5, pp. 724–739, (Sep. 1994).

Weber et al., *1D– and 2D–Sparse–Array–Optimization*, Instrumentation Science and Technology, vol. 27(4), pp. 235–246, (1999).

S.W. Smith, H.G. Pavey, and O.T. von Ramm, "High speed ultrasound volumetric imaging system—part I: Transducer design and beam steering," *IEEE Trans. Ultrason., Ferroelectric., Freq. Contr.*, vol. 38, pp. 100–108, 1991.

R.E. Davidsen, J.A. Jensen, and S.W. Smith, "Two Dimensional random arrays for real time volumetric imaging" *Ultrasonic Imaging*, vol. 16, pp. 143–163, 1994.

S.W. Smith, R.E. Davidsen, S.D. Emery, R.L. Goldberg, and E.D. Light, "Update on 2–D array transducers for medical ultrasound" in *Proc. IEEE Ultrasonic Symposium.*, (Seattle, WA), pp. 1273–1278, 1995.

E.D. Light, R.E. Davidsen, J. Fiering, T.A. Hruschka, and S.W. Smith, "Progress in two–dimensional arrays for real time volumetric imaging," *Ultrasonic Imaging*, vol 20, pp. 1–15, 1998.

O.T. von Ramm, S. . Smith, Thurston, "Grey scale imaging with complex TGC and Transducer arrays" *Application of optical Instrumentation in Medicine*, vol. 4, pp. 266–270, SPIE Belingham, WA, 1975.

Frederick Kremkau, "Diagnostic Ultrasound: Principles Instruments, and Exercises", *W.B. Saunders publishing*, Chapter 3, p. 69–125, Copyright 1989.

J.L. Schwartz and B.D. Steinberg, "Ultrasparse, ultrawideband arrays", *IEEE Trans. Ultrason., Ferroelect., Freq. Contr.*, vol. 45, nO. 2, pp. 376–393, Mar. 1998.

J.T. Yen, J.P. Steinberg, and S.W. Smith, "Sparse 2–D array design for real time rectilinear volumetric imaging", *IEEE Trans. Ultrason., Ferroelect., Freq. Contr.*, vol. 47, pp. 93–110, Jan. 2000.

O.T. von Ramm, "2–D arrays", in *Proceedings of Ultrasonics International 1999 j with World Congress on Ultrasonics*, Ultrasound in Med. & Biol., vol. 26, Supplement 1, pp. S10–S12, 2000.

S.I. Nikolov and J.A. Jensen, "Application of different spatial sampling patterns for sparse array transducer design", *Ultrasonics*, vol. 37, No. 10, pp. 667–671, 2000.

T.R. Nelson, D.H. Petorius, A. Hull, M. Riccobana, M.S. Sklansky, and G. James "Sources and impact of artifacts on clinical three–dimensional ultrasound imaging", Ultrasound Obstetrics & Gynecology, vol 16, pp. 374–383, 2000.

* cited by examiner

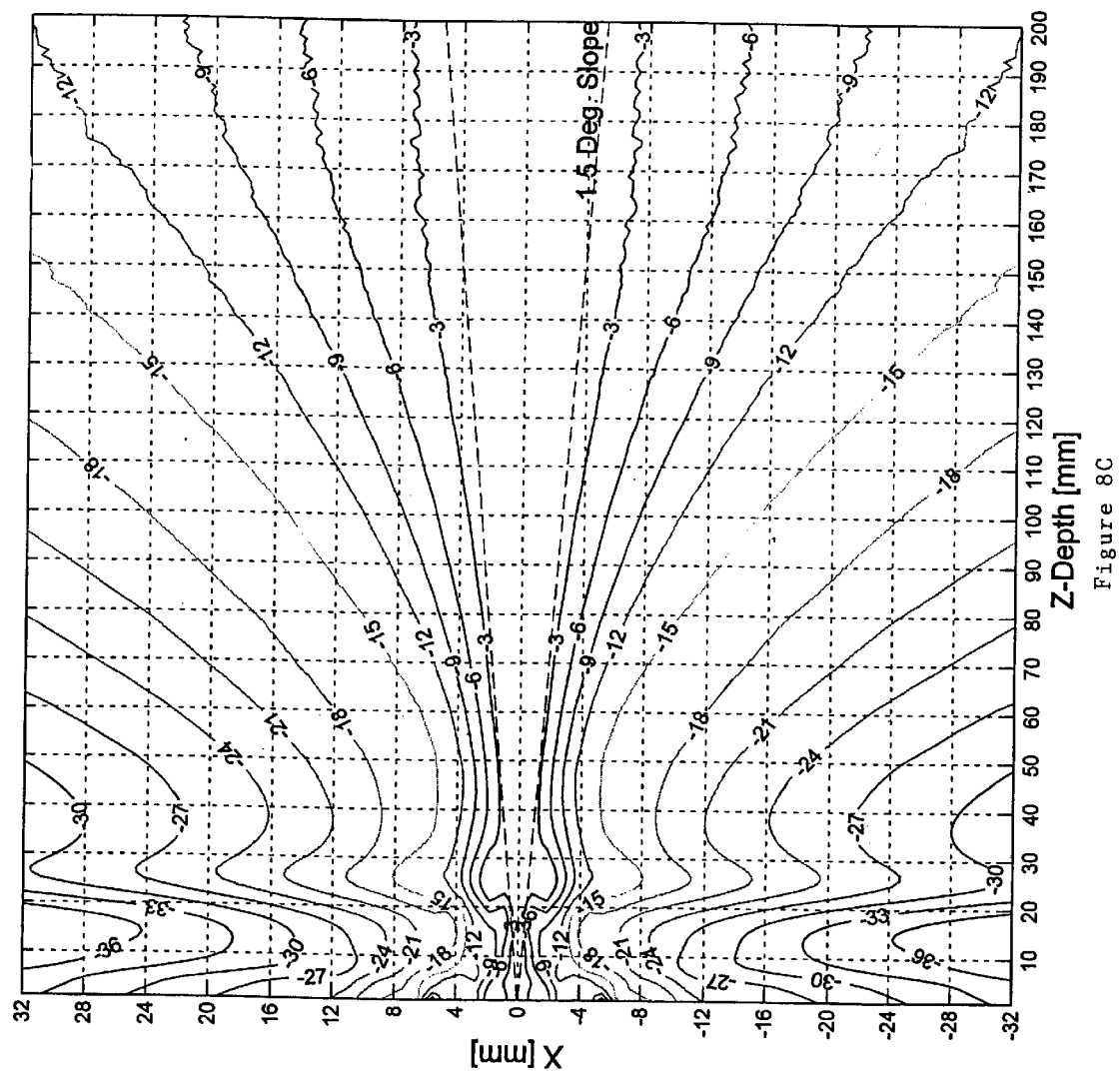

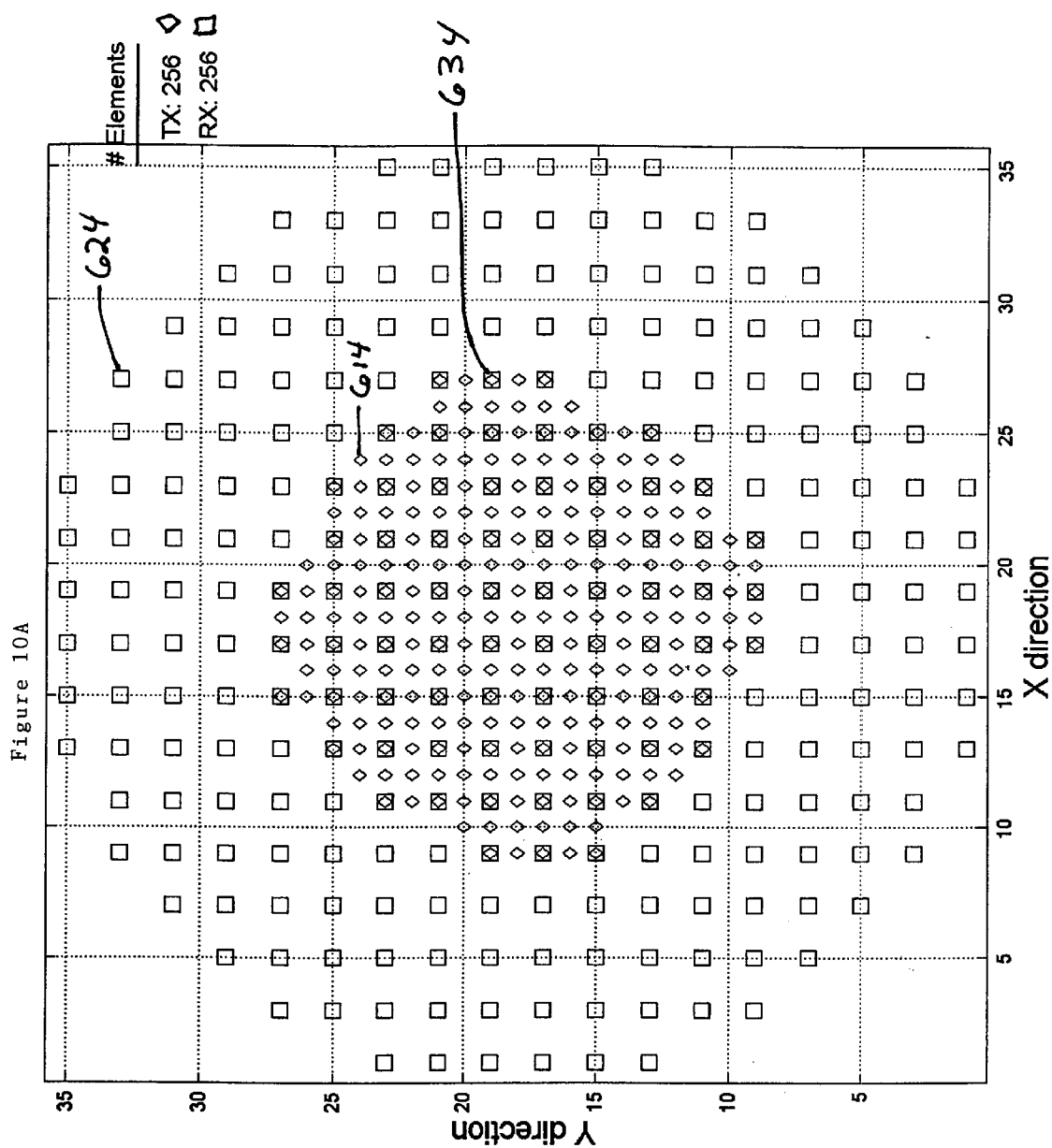

TWO-DIMENSIONAL ULTRASONIC ARRAY WITH ASYMMETRIC APERTURES

This invention was made with government support under grant number R44 HL57111 awarded by National Institute of Health ("NIH"). The Government has certain rights in the invention.

GENERAL

For the convenience of the reader, applicant has added a number of topic headings to make the internal organization of this specification apparent and to facilitate location of certain discussions. These topic headings are merely convenient aids and not limitations on the text found within that particular topic.

In order to promote clarity in the description, common terminology for components is used. The use of a specific term for a component suitable for carrying out some purpose within the disclosed invention should be construed as including all technical equivalents which operate to achieve the same purpose, whether or not the internal operation of the named component and the alternative component use the same principles. The use of such specificity to provide clarity should not be misconstrued as limiting the scope of the disclosure to the named component unless the limitation is made explicit in the description or the claims that follow.

FIELD OF INVENTION

This invention relates to 2D and 3D ultrasound phased array imaging systems for transmitting and receiving ultrasound energy. In particular, this invention relates to an improved sparse array structure that provides an effective aperture and radiation pattern comparable to that of a dense array having a far greater number of array elements. The preferred embodiment of the present invention uses separate arrays of transmit and receive elements and does not employ dual-use "shared transmit/receive elements". The use of two sets of elements allows for a very simple receive buffer to be placed in the head of the transducer and allows the transducer to utilize different transducer optimization between transmit and receive elements. One such case would be the use of two distinct frequencies for harmonic processing and other advantages.

BACKGROUND OF THE INVENTION

This invention adds to the body of work of image processing. Much of the interest and the earlier work has been in the field of medical image processing. FIG. 1 introduces the components of a medical imaging device 100. The medical imaging device comprises a main body 104 connected to a display 108 and various input devices such as a keyboard 112. A cable 116 containing a set of wires 120 connects an array 124 of transducer elements 128 in the instrument head 132 to the main body 104.

In medical imaging, the array of transmit elements 128 sends coordinated pulses of energy into the body. The energy bounces back in various directions as the transmitted energy hits the various surfaces of items within the body. The goal is to measure the energy that reflects back and use the measurements to deduce information about the tissue within the body. Most people know that the thunder from a single clap of lightning is heard by people in a village at different times depending on the relative position of the various observers to the lighting. The same principle applies in imaging in that there is information in not just the amount of energy received by the receive elements but in the delay between the transmission of the energy and the receipt of the echo.

In order to get useful information, there are many transmission elements and many receive elements. Timing delays are used so that elements at different distances from a particular piece of the target can be used collectively to form an image of that piece of the target.

This invention builds on prior concepts and addresses the never-ending quest to get more for less. In this case, "more" means higher resolution images with less artifacts. In this context, "less" means using fewer resources such as fewer devices to transmit or receive the measurement signals, and fewer resources to coordinate, control the devices, and process the information acquired from the receive devices.

The goal is to get the information content that is close to as good as would be obtained from a large fully-populated array of shared transmit/receive elements set out in n rows and n columns while using much less than n×n elements. Such an array with fewer than n×n elements is called a sparse array.

One improvement in the search for getting more for less is described in U.S. Pat. No. 5,537,367 to Lockwood et al. for Sparse Array Structures. The Background of the Lockwood patent sets forth the problem.

Arrays of transducers are used to transmit and/or receive electromagnetic or acoustic energy over a specified region of space (the target).

A portion of the energy that is transmitted bounces back each time the energy wave reaches a new surface in the scanned material.

The arrays of elements are controlled with phase shifts (timing delays) and possibly by weighting so that signals sent to or received from the target constructively interfere while signals outside of the target destructively interfere.

The radiation pattern is a plot of the amplitude of the signal transmitted or received by the array as a function of the position in space.

The radiation pattern of an array indicates how well the array achieves the desired constructive and destructive interference. The radiation pattern is usually plotted in polar coordinates at a given distance in front of the array.

The transmit/receive radiation pattern is a combination of the transmit radiation pattern and the receive radiation pattern. The transmit/receive radiation pattern gives a measure of the sensitivity and resolution with which the array will be able to detect objects.

An example of a typical transmit-receive radiation pattern is shown in FIG. 2. The radiation pattern consists of a prominent main lobe 150 and a number of secondary lobes 154. The main lobe corresponds to the desired region in space over which energy will be transmitted and from which energy will be received.

The width of the main lobe 150 is inversely proportional to the width of the array and determines the resolution of the array. In other words, a larger array has a narrower main lobe 150 and has better resolution. Lobe width is often described as the distance between the lobe's "shoulders".

The secondary lobes 154 are caused by imperfect destructive interference outside of the target area and result in the transmission and reception of unwanted energy. The energy received from side lobes does not represent information about the target region and makes it more difficult to detect subtle differences in the target.

Thus, it is a goal when designing an array to minimize the width of the main lobe (to increase resolution) while minimizing the secondary lobes.

One way to get a higher quality image is to add transducer elements to make a larger fully-populated array. Adding array elements has benefits. Experience has shown that the array should be at least as wide as 20 times the wavelength of sound at the transducers' center frequency in order to focus sharply to give high imaging resolution.

However, there are practical limits on how many array elements can be added. The costs associated with adding array elements include:

1) the cost of the additional transmit or receive element,
2) the cost of the circuits to control or process the information from the element,
3) the problem of cross coupling that occurs when too many wires connected to the various transmit and receive elements are running through the cable connecting the head to the main body of the measurement instrument,
4) the undesired weight added to the measurement instrument head; and
5) if transducers are shared for both transmitting and receiving, it will require transmit/receive switching with its added costs and size.

PRIOR ART SOLUTIONS AND THE CONSEQUENCES

A) Increase the Spacing Between Elements

One solution to the desire to have a wide array but control the number of elements would be to use a fully populated array but simply space the elements with greater gaps between them. However, whenever the spacing of elements in a phase array transducer exceeds approximately one half of the wavelength of sound used by the element, the periodic spacing of the elements causes additional unwanted side lobes known in the art as grating lobes.

Since it is desirable that the array should be at least 20 wavelengths (20 lambda) wide in order to provide high imaging resolution and it is desirable to have the elements spaced at no more than 0.5 lambda, a fully populated 20 lambda array would be an expensive proposition. Such a system would need to be capable of pulsing 1600 transmit elements and operate 1600 receive elements.

B) Vary the Spacing to Reduce Grating Lobes

The grating lobes can be reduced by having variations in the spacing between elements. It is difficult to design such aperiodic arrays in a way that minimizes the secondary lobes. Attempts to use random connection patterns broke up the strong grating lobes into numerous small grating lobes. This avoided strong ghost images but led to a low contrast image as the many small grating lobes picked up echoes from many different directions and produced a visible background clutter.

Others have tried a vernier approach with different uniform patterns for overlapping transmit and receive arrays. For example, one might try to use every other element for transmit and every third element for receive. There were attempts to get the receive grating lobes to be non-aligned with the transmit grating lobes. One scheme was to design a vernier array with the transmit grating lobes falling at angles corresponding to the nulls in the receive beam pattern. While the vernier approach was an improvement over the random pattern, the result still had ghost images.

C) Apodization

The solution chosen in the Lockwood patent is a process known as apodization. Apodization is the process of weighting the individual array elements in an attempt to optimize the array performance. Apodization is not without costs. Apodization causes a wider main beam and reduces the signal to noise ratio. The reduced signal to noise ratio is a consequence of attenuating the signals that are already small before attenuation.

An example of a sparse array designed for use with apodization is included as FIG. 3. This figure shows an array disclosed in the Lockwood '367 patent.

This two dimensional array has 69 receiver elements and 193 transmit elements. The array was designed with two overlapping arrays, one for transmit and one for receive. The points where transmit and receive arrays overlap use combination shared transmit/receive elements and the associated circuits to enable the sharing of the transmit/receive capabilities of the element.

For example, a shared transmit/receive element shares one wire in the cable that goes from the head to the main body of the measurement instrument. Multiplexer switches must switch the connections from the high voltage pre/amp needed for the transmit portion of the element and low voltage pre/amp needed to operate the receive portion of the element.

In accordance with the Lockwood method, the elements were weighted with an apodization function (in this particular case, it was a cosine apodization).

D) Disadvantages of the Method Proposed by Lockwood

The method taught by the Lockwood patent suffers from several drawbacks.

The first drawback is the previously described complication associated with having to use an apodization scheme to weigh the individual transmit and/or the individual receive elements in order to obtain a suitable radiation pattern.

In addition to the drawbacks from the use of apodization, there are drawbacks from the use of the shared transmit/receive elements that are necessitated by the overlap between the receive and transmit arrays. The drawbacks from the use of the shared use elements go beyond the need for multiplexing switches and the need for coordinating the high speed switching of the circuits and wire from one function to the other.

One drawback is the need to protect the ultra low voltage receive circuitry from the high voltages used by the transmit circuit. This problem does not exist with a sparse array using dedicated transmit elements that are separate from the dedicated receive elements. A transmit element that does not share circuitry with a receive element can operate at a higher voltage (on order of magnitude of tens or hundreds of volts) without risk of damaging the sensitive receive circuitry which operate on voltages from 2 to 8 orders of magnitude less than the transmit circuits (on the order of micro-volts). Thus, there is less need for circuitry to isolate the high voltage transmit circuits from the low voltage receive circuits.

Another drawback is that the shared transmit/receive element operates on a single frequency range and there may be reasons why it would be advantageous for the transmit and receive elements to operate on different frequency ranges. The prior art has found advantages in certain imaging techniques that use one frequency for the transmitted energy and measure the received energy at another frequency. This is called harmonic imaging. The receive frequency is often a multiple of the transmit frequency but it could be a sub-harmonic (such as ½ of the transmit frequency) or a fractional harmonic (such as 3/2 the transmit frequency). When using a shared transmit/receive element intended to transmit a first frequency and receive back a different frequency, one has difficulty optimizing both the transmit and the receive functions as there is only one transducer crystal with a single range of transducer frequencies.

E) Annular Arrays and Steerable Limited Diffraction Beams

One way of characterizing two-dimensional ultrasonic arrays is to divide arrays into linear arrays and annular arrays. Linear arrays have elements arranged in a line or a grid pattern. These individual elements can be activated to form regions of active elements in shapes such as the circles, rings, or polygons.

In contrast, annular arrays have a series of ring shaped transducers that are arranged in a concentric pattern. The center of the annular array can be a circular transducer. Instead of having hundreds of separately controlled elements, an annular array may have simply a center element and three annular elements surrounding the center. The annular arrays thus have fewer elements and this would seem to be an advantage. However, it is actually a disadvantage as having fewer elements provides less opportunity for control through time delays for pulsing and measurement windows, weighting, and other processing tools.

As mentioned, one noted shortcoming with annular arrays is that the beams cannot be electronically steered by introduction of time delays as is commonly done in linear arrays. Thus, steering must come from mechanically scanning the head or from a mechanical wobble that moves the head. Mechanical movement has a number of shortcomings relative to electronic steering, such as limitations from inertia, problems with wear, and the inability to collect data in a pattern that is independent of the mechanical properties of the mechanical equipment.

The prior art has worked with annular arrays to obtain approximate a Bessel beam with a large depth of field and depth-independent properties.

One recent paper by J. Lu and J. F. Greenleaf titled "A Study of Two-Dimensional Array Transducers for Limited Diffraction Beams" appeared in the *IEEE Transactions of Ultrasonic, Ferroelectrics and Frequency Control* at vol. 41, U.S. Pat. No. 5,724,739, September 1994 described the approximation of an annular array by use of elements in a two-dimensional linear array so that electronic beam steering could be used to steer the annular regions of elements.

This paper suggested the use of 14 rings excited according to a Bessel function weighting pattern. The goal would be to retain the favorable focal qualities of a limited diffraction beam while adding the beam steering capabilities of a two-dimensional array.

Instead of using annular (single element) rings, each ring would be comprised of a set of transducer elements used for both the transmit and the receive functions. The entire set of transducers for a ring would be electronically connected so that all the elements in a particular ring would be driven by the same waveform. The paper suggests the use of a series of elliptical shaped rings, instead of circular rings, in order to compensate for the reduction in effective aperture from steering the beam. As the beam is steered further from the center, the device switches to progressively larger elliptical shaped-rings to offset the decrease in effective aperture from the increase in steering angle.

The advantage of this approach is an extended transmit focal zone that is characteristic of Bessel beams or other limited diffraction beams.

One limitation of this approach is the use of weighting or apodization because of the cost of the added circuit complexity. Another, limitation is the large number of elements required for this scheme. Even spaced at the relatively large interelement spacing of 1.5 lambda, the elliptical array of 29.2 lambda by 41.2 lambda requires 1700 shared transmit/receive elements.

Even with the extensive work in the prior art, there remains a need for a two-dimensional sparse array that provides a high quality image from a relatively small total number of transmit and receive elements.

It is an object of the present invention to provide a two-dimensional sparse array that provides a high quality image from a relatively small number of transmit and receive elements and overcomes limitations found in prior art solutions.

These and other advantages of the present invention are apparent from the drawings and the detailed description that follows.

BRIEF SUMMARY OF THE DISCLOSURE

This disclosure a novel sparse array that uses a small fraction of a fully populated array but yields a radiation pattern that is suitable for high quality medical imaging.

More specifically, the disclosed sparse array uses an inner array of transmit elements and an outer array of receive elements. In the preferred embodiment, the system using this sparse array does not use apodization for weighting. In the preferred embodiment, the system does not use shared transmit/receive elements and thus avoids the costs and compromises inherent in using shared transmit/receive elements.

In the preferred embodiment, the elements are spaced at no more than approximately 0.5 lambda of a center frequency for the elements. This inter-element spacing applies to both the scan (azimuth) and elevation directions.

The preferred embodiment discloses arrays with a transmit aperture that is a narrow aperture (broad beam) to "illuminate" the target area with a receive aperture that is a large aperture (narrow focus) which is well suited to use in applications using parallel processing.

DETAILED DESCRIPTION OF DISCLOSED EMBODIMENTS

Figure 4:
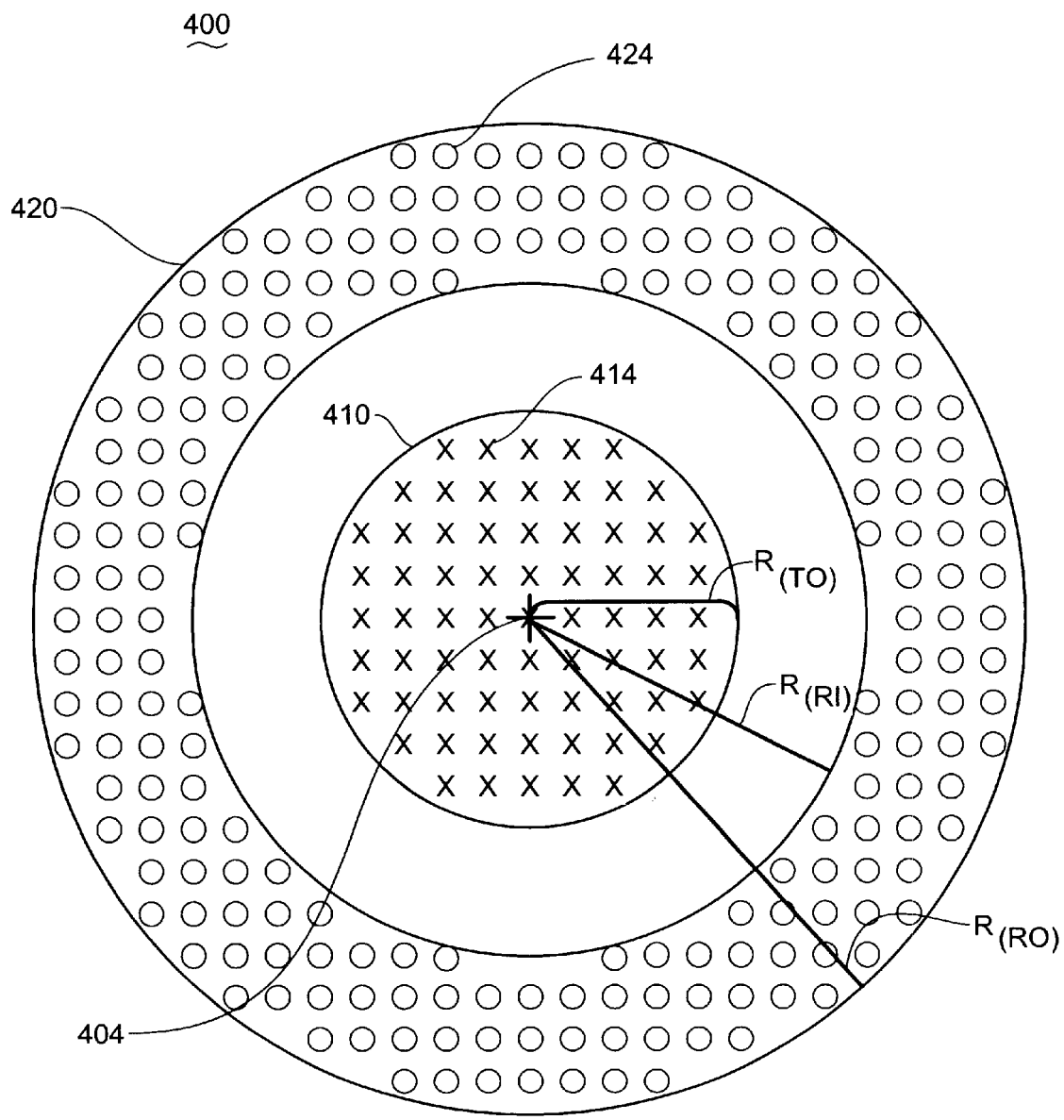
FIG. 4 illustrates a first embodiment of the present invention having an inner transmit array and an outer annular receive array.

FIG. 4 describes a first embodiment of the present invention.

The sparse array 400 is centered around a center axis 404. (Compare with FIG. 7 that has two centers, one for receive and one for transmit.) The sparse array has an inner transmit array 410 and an outer receive array 420. The inner transmit array is comprised of a series of transmit elements 414. The transmit array is located in the region defined by a circle with midpoint at the center axis 404 and outer perimeter defined by radius $R_{(TO)}$ 418. In the preferred embodiment the region of the transmit array is fully populated, that is the transmit elements are spaced at no more than approximately 0.5 lambda apart.

The outer receive array 420 is comprised of a series of receive elements 424 located in an annular area around center axis 404 between the radius R(Ti) and $R_{(TO)}$. In the preferred embodiment the region of the receive array is fully populated, that is the receive elements are spaced at no more than approximately 0.5 lambda apart.

Note that inner array is arranged in a circle and the outer array is arranged in an annular shape. Circles are desirable shapes as circles have two favorable qualities. A circle is the most efficient shape for arranging an area of elements. The symmetry of a circular array means that the array can be steered in any direction and provide the same result as the array steered an equivalent amount in any other direction. This can be restated as circular arrays differ from rectangular arrays in that a circular array produces symmetric results within a conical steering volume.

The sparse array 400 can be located on a concave surface, a convex surface or on a flat surface. The use of beam forming techniques for use with an array located on a flat surface is well-known in the art.

The use of a smaller inner transmit 410 is effective to transmit energy on the target in much the same way as a floodlight lights an area.

The wide outer receive array 420 has characteristics analogous to a spot light in that it is a narrower focused beam. Of course, the receive array works to receive rather than to transmit, but the shape analogy holds as the wide diameter receive array has a wide effective aperture and thus produces a relatively high resolution image. Through techniques known in the art, the receive array can operate through parallel processing to look at an array of small segments of the target in response to a single transmit from the transmit array. For example, the receive array can process 16 receive signals in parallel from a four by four array of receive segments. Parallel processing of signals is well known in the art. See e.g. U.S. Pat. No. 5,546,807 to Oxaal et al. or U.S. Pat. No. 4,596,145 to Smith et al.

The improved sparse array reduces the grating lobes associated with periodic arrays so that the grating lobes for both the transmit and receive arrays do not have strong grating lobes at angles well away from the main lobe so that ghost images are not a distraction on the displayed image.

Every deviation from a fully populated array has some trade-offs. This design leads to a main lobe with shoulders that are wider than could be achieved with a fully populated array. However, the increase in contrast achieved by the reduction of noise from grating arrays more than offsets the slight loss of resolution from the broader shoulders of the primary lobe.

While it would be possible to eliminate a few of the center transmit elements from the transmit array, removing more than a few elements is thought to be undesirable in that it would tend to increase the height of the sidelobes and decrease the transmit amplitude. Likewise it is possible to operate the array with a certain fraction of "dead" elements without serious degradation of signal quality.

The most preferred embodiment uses separate transmit and receive elements which helps isolate the sensitive receive elements from the high voltage of the transmit elements, and allows the receive transducers to be optimized to operate at a center frequency that is different from the center frequency used for the transmit elements. This is useful for harmonic imaging. In the preferred embodiment, the spacing of the elements would be at 0.5 lambda which means that the distance between receive elements would be different than the distance between transmit elements as the two sets of elements will use different center frequencies.

The use of separate transmit and receive elements is also useful in facilitating the introduction of low cost receive buffers in the head 132 of the transducer. This is useful because it buffers the small signals received from the transducer head and prevents excessive attenuation as the signal passes from the head 132 to the main body 104.

F) The Relationship Between $R_{(TO)}$ and $R_{(RI)}$

By having a transmit array that does not overlap with the receive array, there is a significant reduction in the number of elements connected to receivers or transmitters.

One way of looking at this is to imagine a system with a transmit array filling a circle defined by radius $R_{(RO)}$. The same circle has an overlapping array of receive elements in the same area and with the same spacing. Compare that with a situation where the same circle was divided into two regions. One region receives only transmit elements, and the other region receives only receive elements. In the second situation there are only about half as many total elements as when the entire circle had two arrays. One way to get this approximately fifty percent reduction in transducer elements is to limit the transmit elements to a region defined by an inner circle of $R_{(TO)}$ and limit the receive elements to an outer annular area defined by $R_{(RI)}$ and $R_{(RO)}$ where $R_{(TO)}$ is slightly less than $R_{(RI)}$.

If this is an acceptable reduction in the number of elements, then $R_{(RI)}$ can be just larger than $R_{(TO)}$. However, many applications will prefer to have fewer elements while keeping the wide effective aperture of the receive array. Thus, most uses of the present invention will include an annular gap between the outside of the transmit array region ($R_{(TO)}$) and the inside edge of the receive array region ($R_{(RI)}$). The width of the annular gap will exceed the spacing between elements within either array so that a map of the array would have a visible gap between the transmit array and the receive array.

The gap has multiple benefits including helping to isolate the transmit signals from the receive signals. Another benefit is that the gap leads to a larger effective aperture of the receive array and thus improves the focal resolution of the receive array.

In one preferred embodiment, the center frequency of the transducers used in the transmit array is at one frequency and the center frequency of the transducers used for the receive array is at a second frequency to optimize the transmit and the receive transducers for use in harmonic imaging.

G) Radial Measurement in Polygonal Configurations

As a practical measure, many arrays of transducer elements are constructed as part of a rectangular grid. The regions of transmit and receive elements are often better described using a series of concentric polygons (sharing the same center point).

Figure 5A:
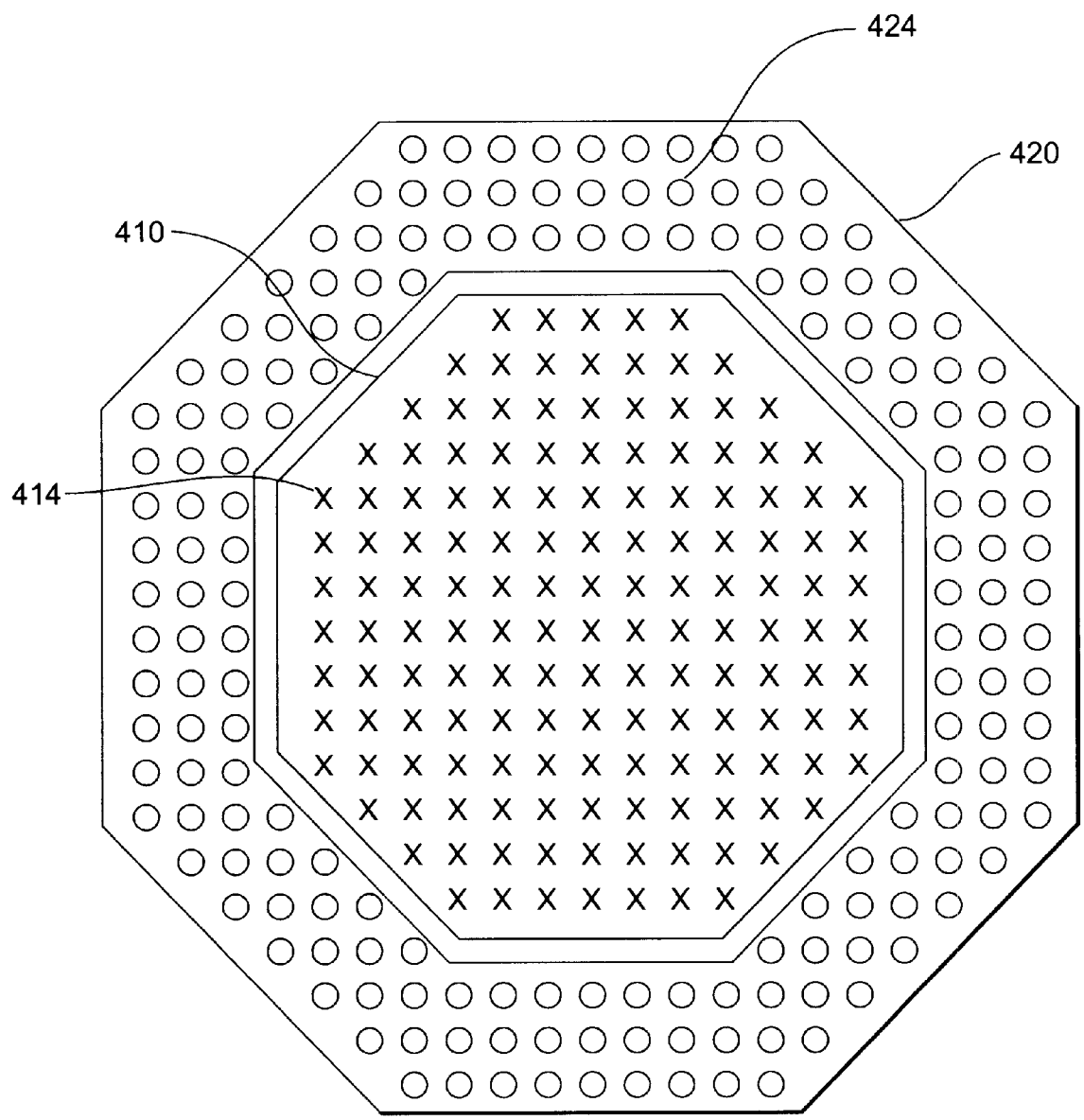
FIGS. 5A and 5B describe the geometry of concentric polygons such as may be used to implement the present invention in lieu of using concentric circles and rings.
Figure 5B:
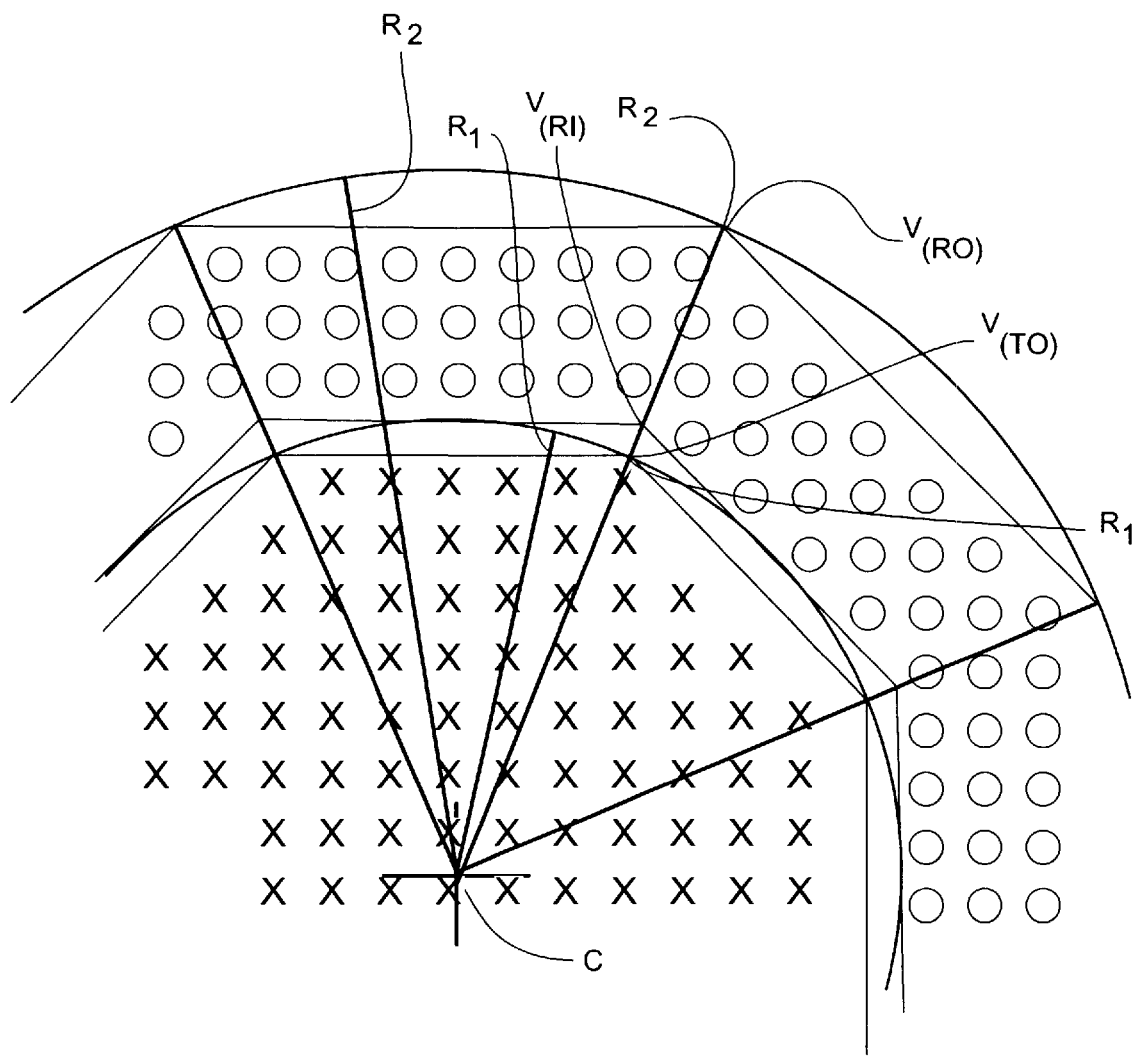

FIG. 5A shows the relationship between concentric polygons and concentric circles. To show additional detail, FIG. 5B shows an enlarged portion of FIG. 5A. In order to focus on the geometry, FIG. 5B excludes the depictions of the individual transmit and receive elements.

Note that as described below-defining the regions of transmit and receive elements using radial measurements does not work precisely when the elements are arranged in concentric polygons with little distance between one polygon and the next.

Thus region containing the transmit array can be described as a polygon defined by the center of the array C with the n vertices of the polygon spaced approximately $V_{(TO)}$ from the center.

The transmit array is surrounded by the receive array that is located in the annular array defined by the inner polygon and the outer polygon. The inner polygon for the receive array is defined by the center of the array and n vertices at a distance $V_{(RI)}$ from the center. $V_{(RI)}$ can be relatively small as shown in FIG. 5 or can be larger so that there is a visible gap in the map of transmit and receive elements.

The outer polygon bordering the receive array is defined by center C and n vertices a distance $V_{(RO)}$ from the center.

Notice that the use of radial measurements to describe a set of concentric polygons leads to a slight imprecision. As shown in FIG. 5B, a zone defined by radial distance $R_1$ passes through the vertices of the polygon containing the transmit elements but also captures a portion of the annular polygon containing the receive elements. Thus, to precisely distinguish the region containing transmit elements from the region containing receive elements for a set of concentric polygons, it may be necessary to define the spaces in terms of distances to the vertices rather than through the use of the more traditional radial distances.

Simulation Results

FIGS. 8, 9, 10, and 11 are sets of simulation results for four different layouts of transmit and receive elements.

Figure 8A:
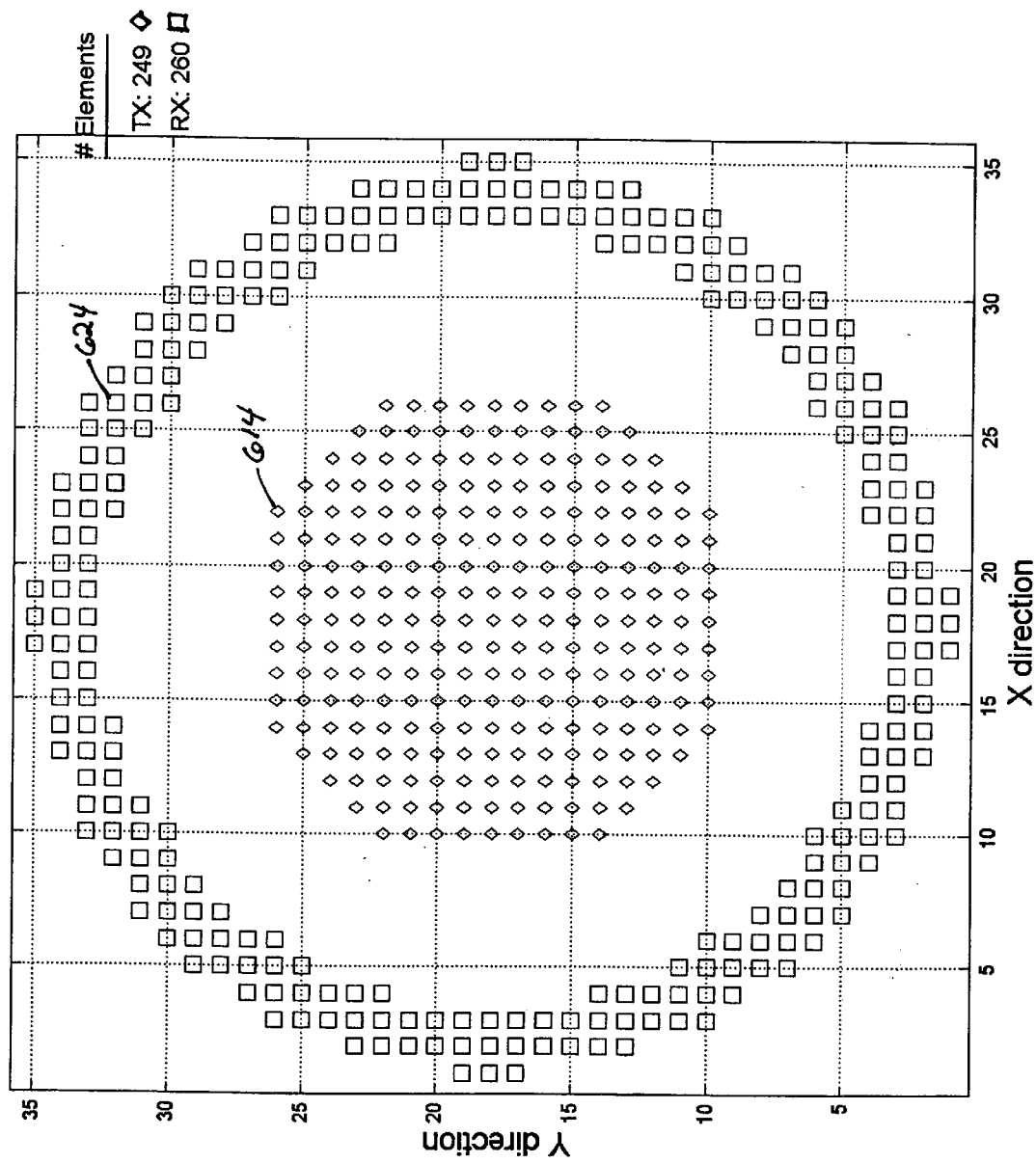
FIGS. 8A, 8B, and 8C show an array of transducers in a bulls-eye pattern along with simulated results that are comparable with that found in FIG. 11 and better than that found in FIGS. 9 and 10.

FIG. 8A shows an arrangement of 249 transmit elements 614 in an octagon within a ring of 260 receive elements 624. The inner octagon and outer ring are separated by a guard band. This arrangement uses a narrow effective aperture to generate a wide transmit beam and couples that with a wide effective aperture for a focused receive beam.

This arrangement has relatively few connected elements and does not use any shared transmit/receive elements. However, the simulation results compare favorably with the results for the arrangements shown in FIGS. 9A, 10A, and 11A although those arrangements use more total elements and make use of shared transmit/receive elements 634.

Figure 8B:
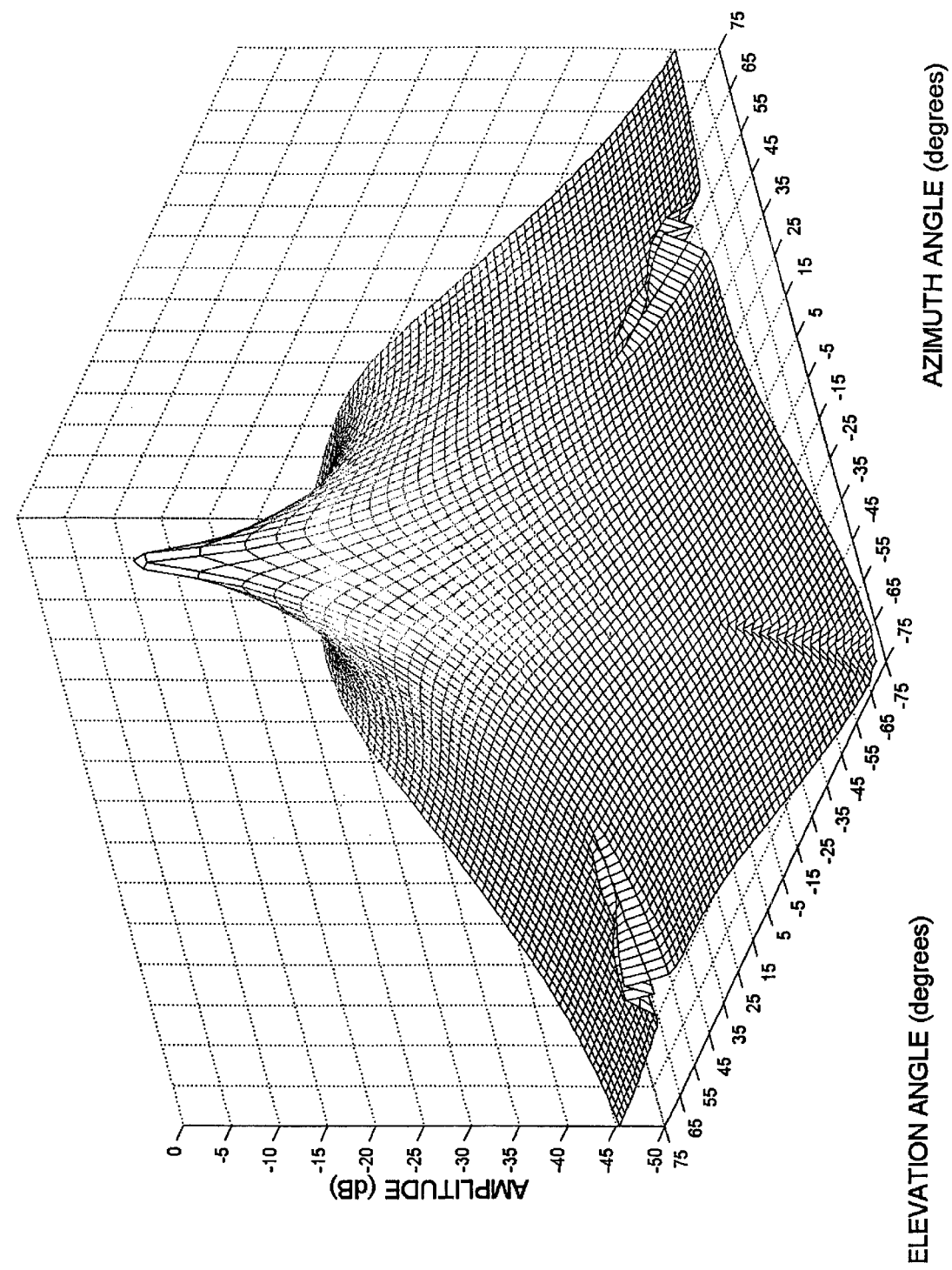

FIG. 8B is a three dimensional plot of amplitude roll off as a function of elevation angle and azimuth angle for simulated results based on the arrangement of elements shown in FIG. 8A. Again this plot is favorable as the plotted results lack any significant lobes. This is significant as significant lobes lead to visual artifacts of various types.

Figure 8A:
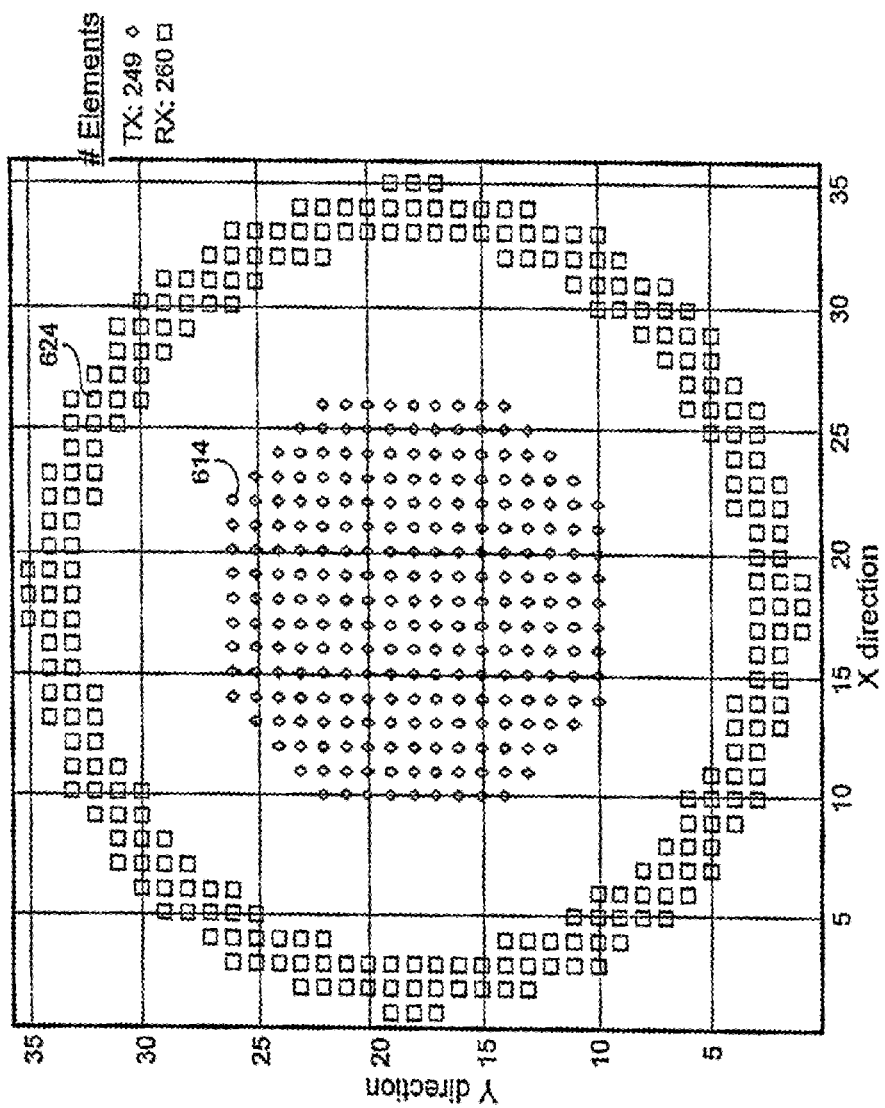
Figure 8C:
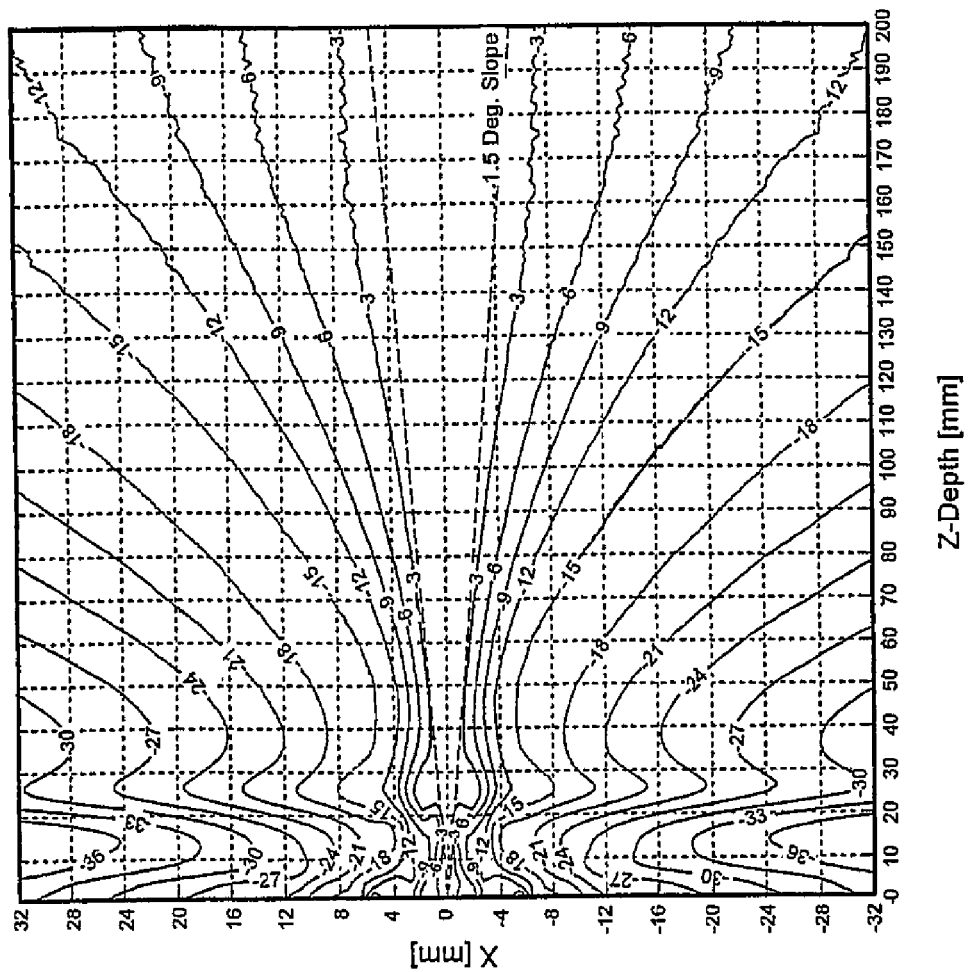
Figure 9A:
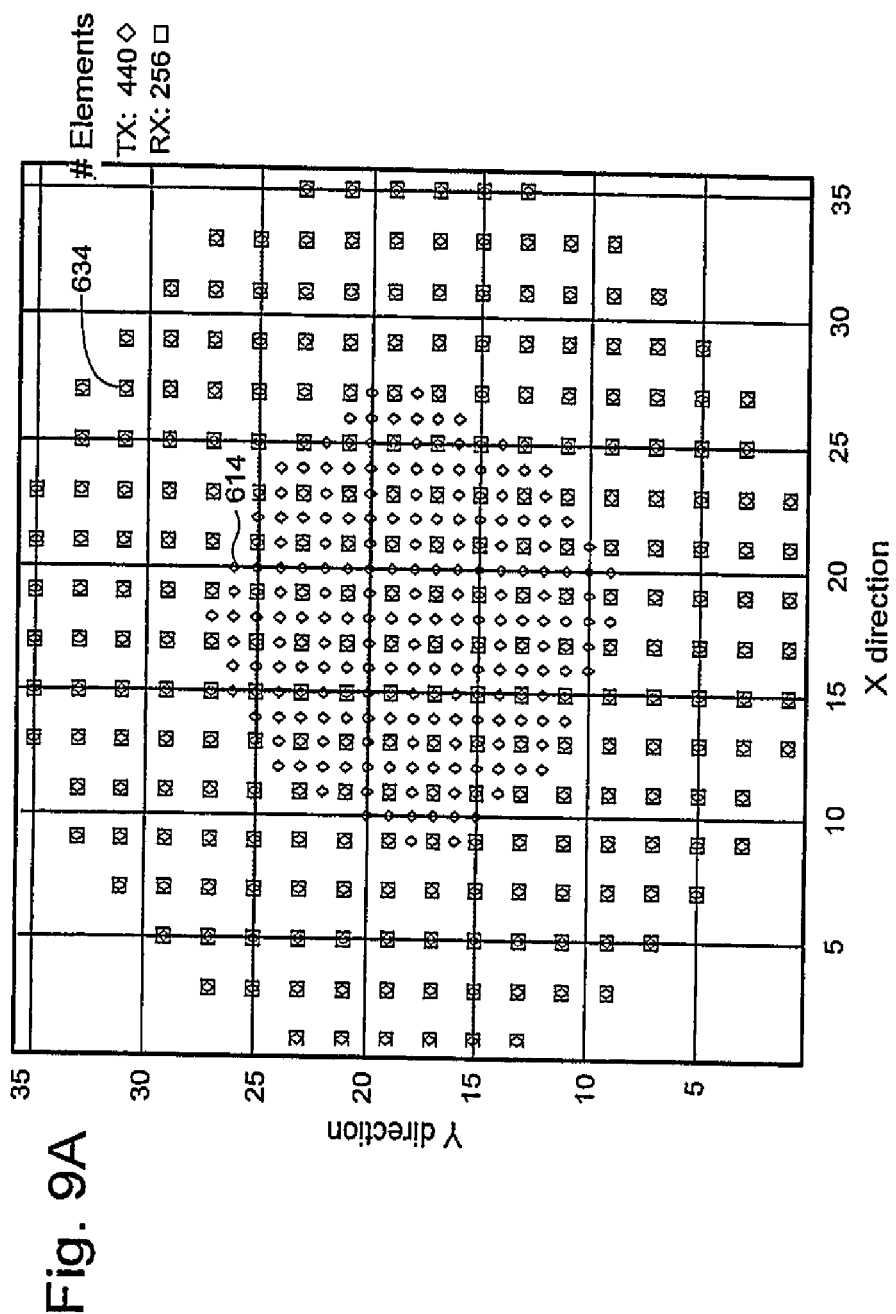
Figure 9B:
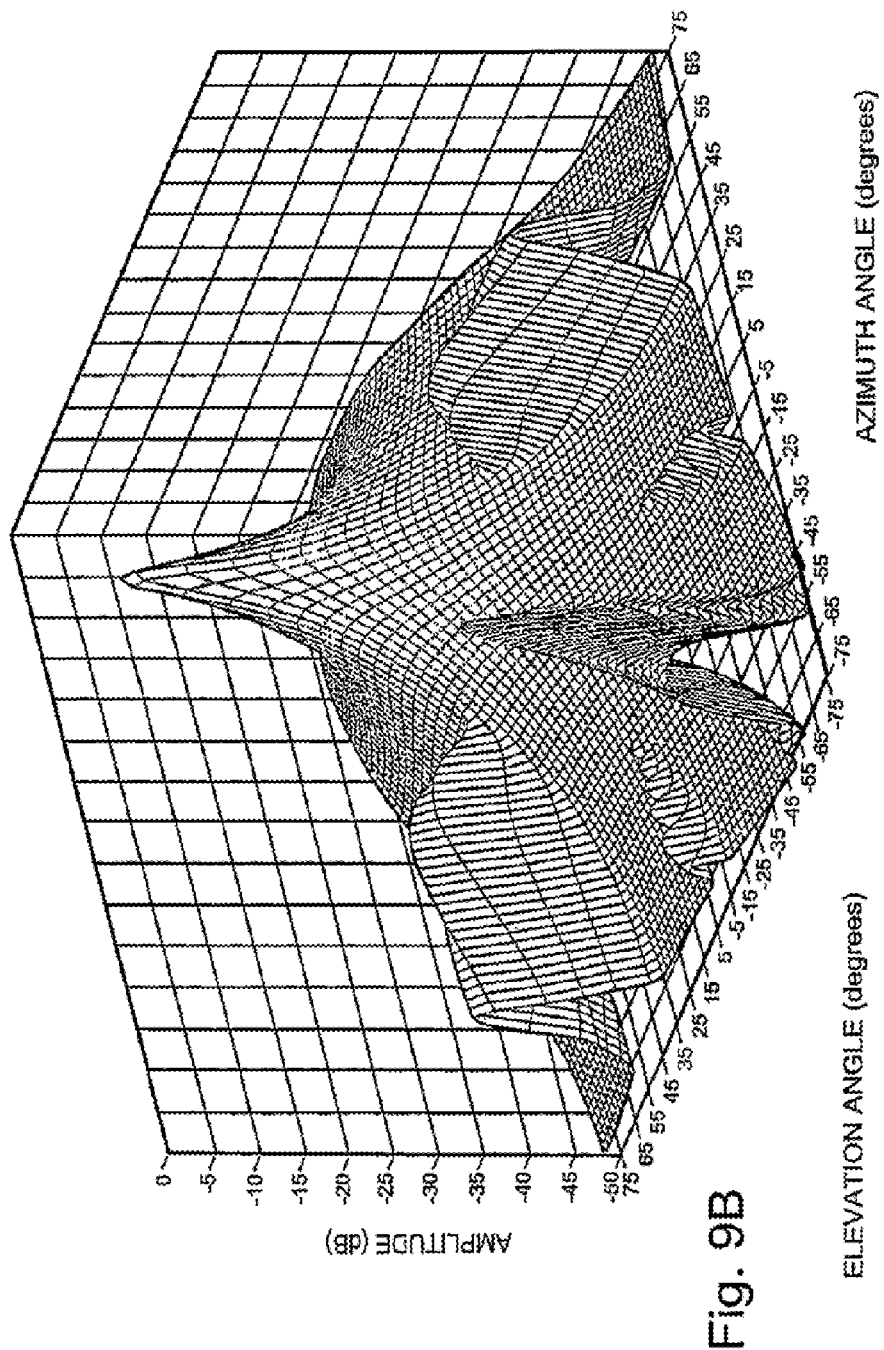
Figure 9C:
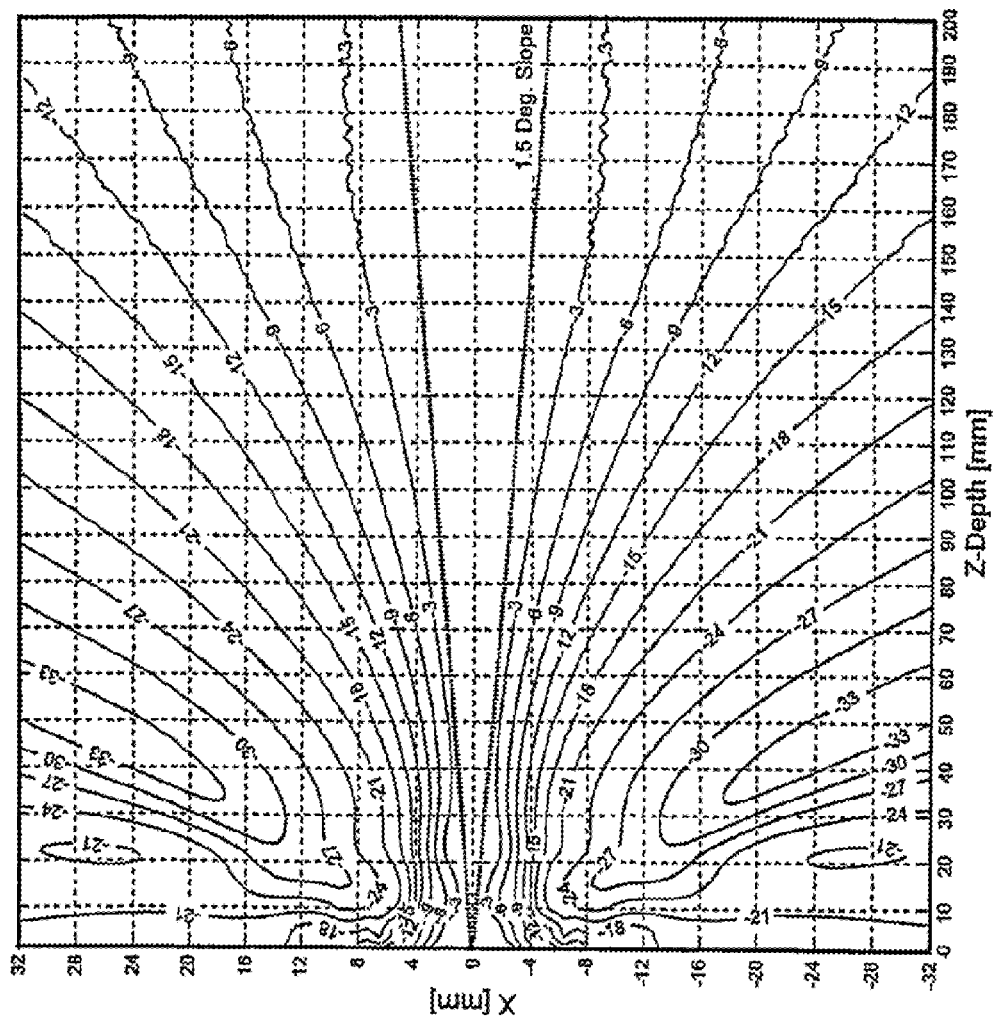

FIG. 8C is a graph of amplitude roll-off as a function of depth for simulated data based on the arrangement of elements shown in FIG. 8A. The desired characteristic here is a relatively narrow region of full amplitude and then a roll off of amplitude. While it may seem useful to have a broad region that provides a full power response, it is actually desirable to get a strong response only from the area being targeted and get attenuated or no response from areas outside of what is targeted. Thus, have a narrow beam pattern is useful for having resolution.

FIG. 8C shows a desirable pattern with a roll off of 3 dB on either side of the 1.5 degree slope reference line.

Figure 9A:
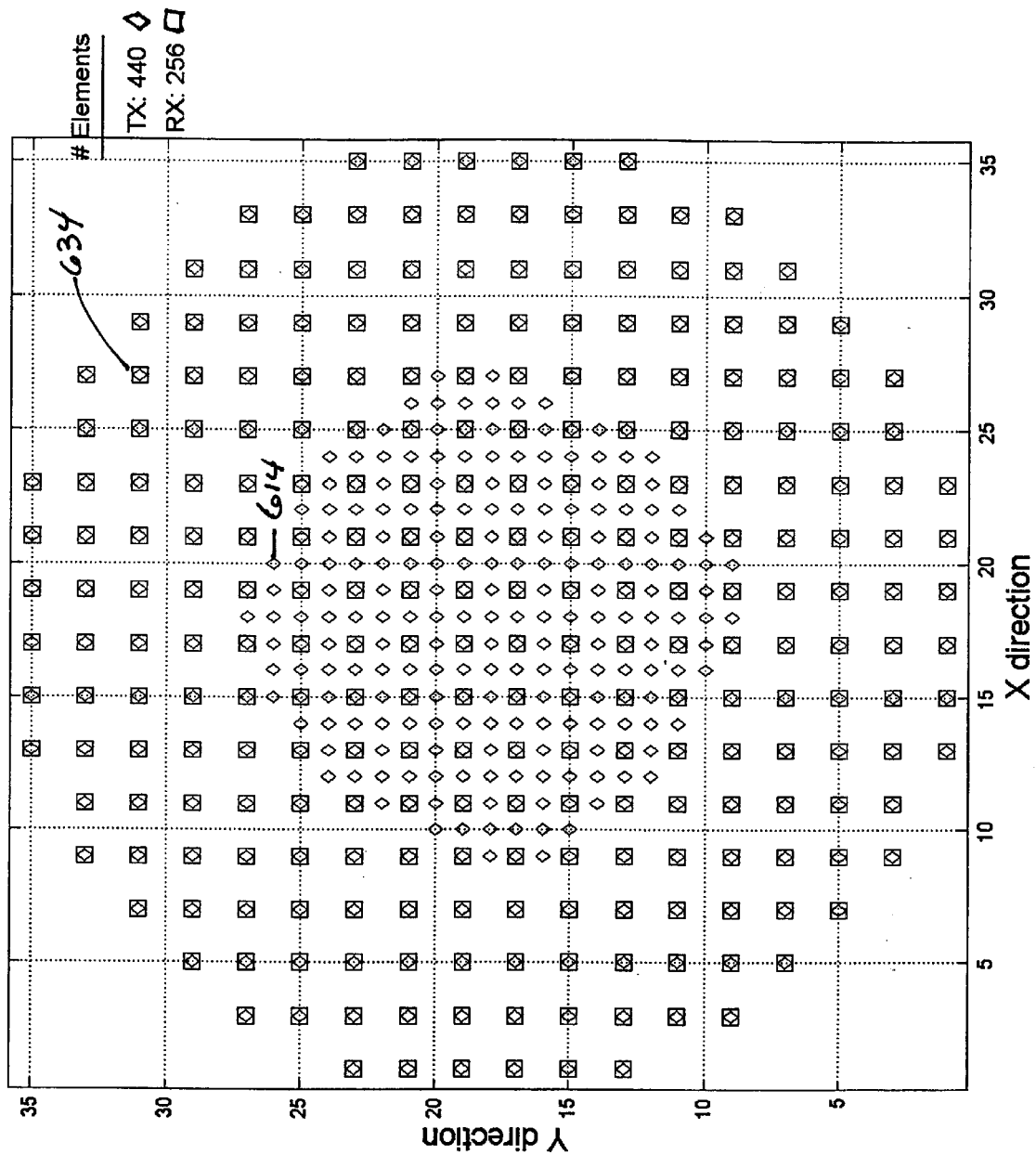
FIGS. 9A, 9B, and 9C show prior art arrays and simulated results from the beam pattern.

FIG. 9A shows an arrangement of elements with approximately the same number of receive elements and far more transmit elements. This vernier array pattern is based on a prior art array used by assignee. This simulation uses sparse array of shared transmit/receive elements 634 augmented by a set of transmit elements 614 in an inner octagon as in FIG. 8A. The transmit elements are spread throughout the entire array but this arrangement has a larger inter-element spacing than used for the receive elements in FIG. 8A. Contrary to what one might guess based on the increased number of total elements, the arrangement of FIG. 9A has major lobes present in the plots of simulated data shown in FIG. 9B.

Figure 9B:
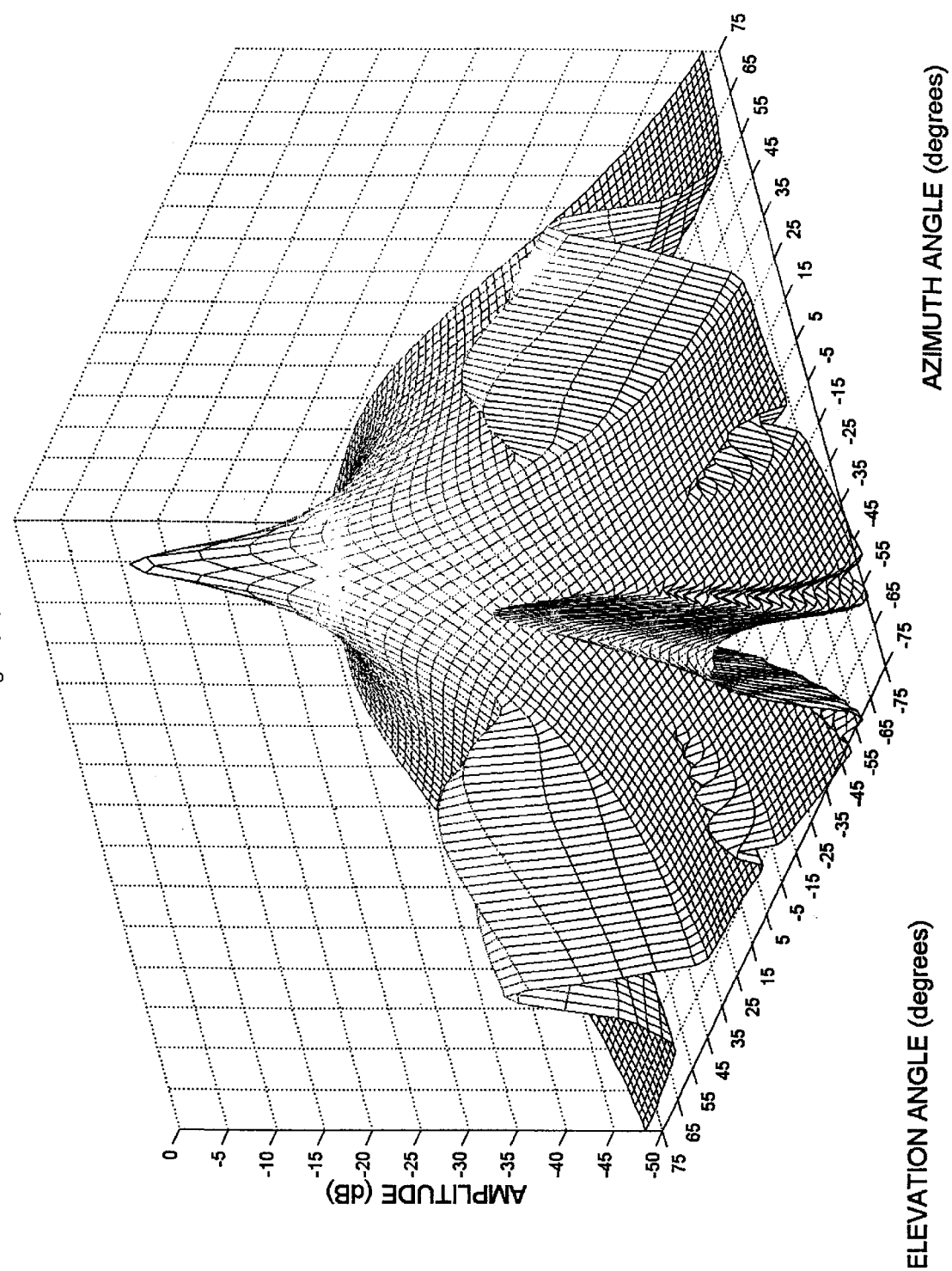
Figure 9C:
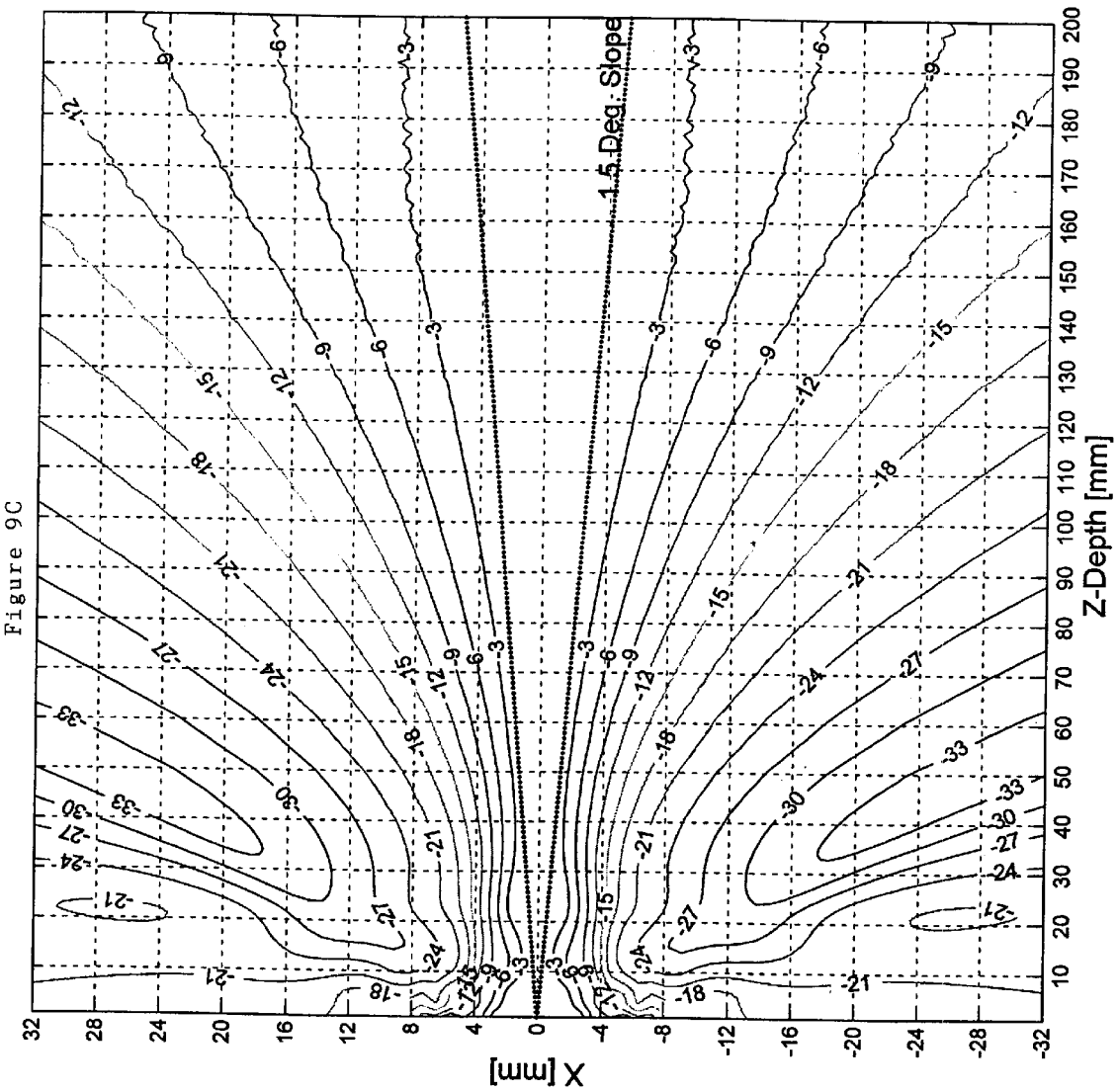

FIG. 9C provides a graph, of roll-off as a function of depth. A careful comparison with the 1.5 degree reference line shows that the 3 dB lines are further apart in FIG. 9C than in FIG. 8C. This shows that the array of FIG. 8A provides better resolution than the array of FIG. 9A.

Figure 10B:
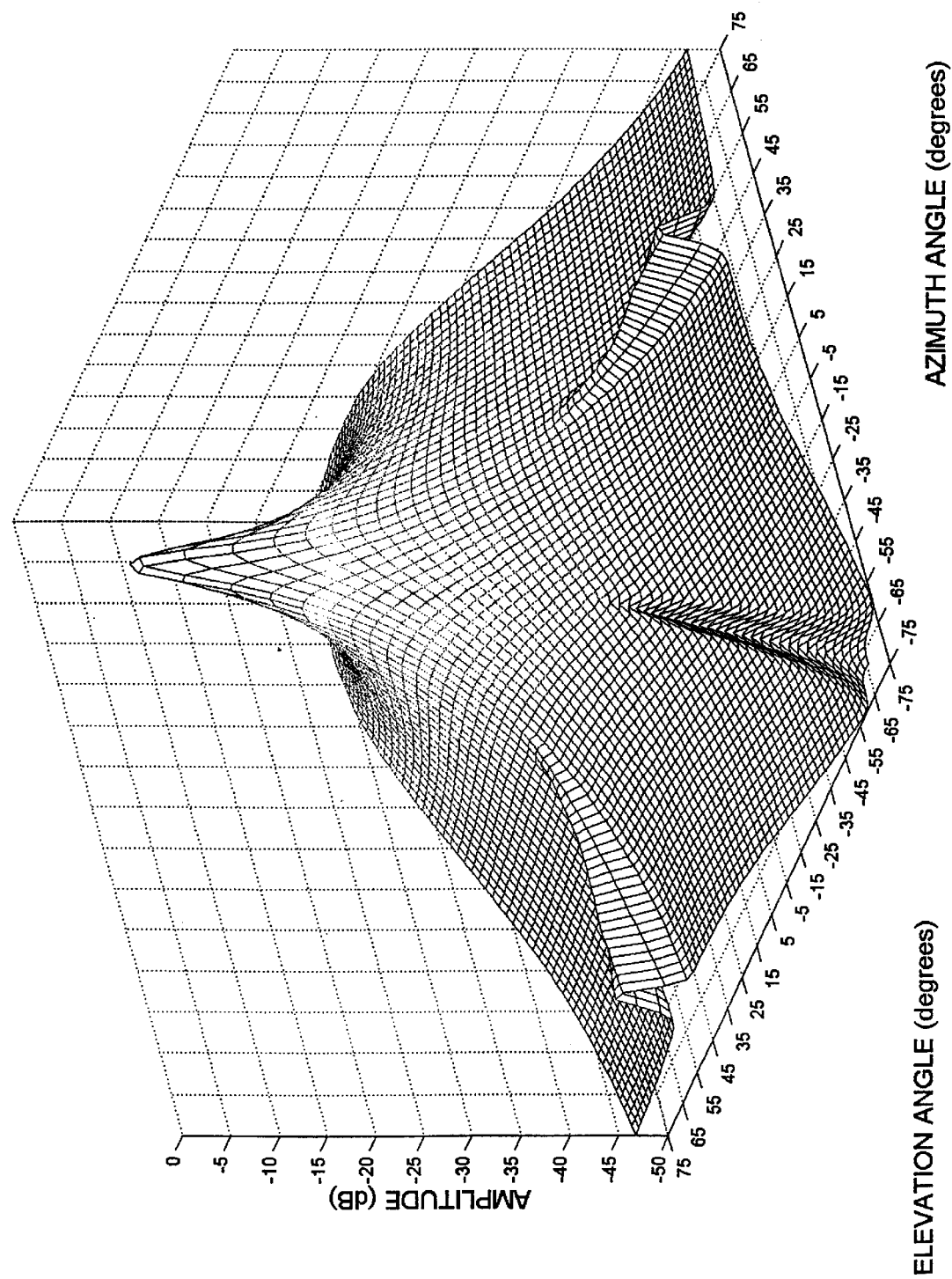
FIGS. 10A, 10B, and 10C show another possible array and simulated results from the beam pattern.
Figure 10C:
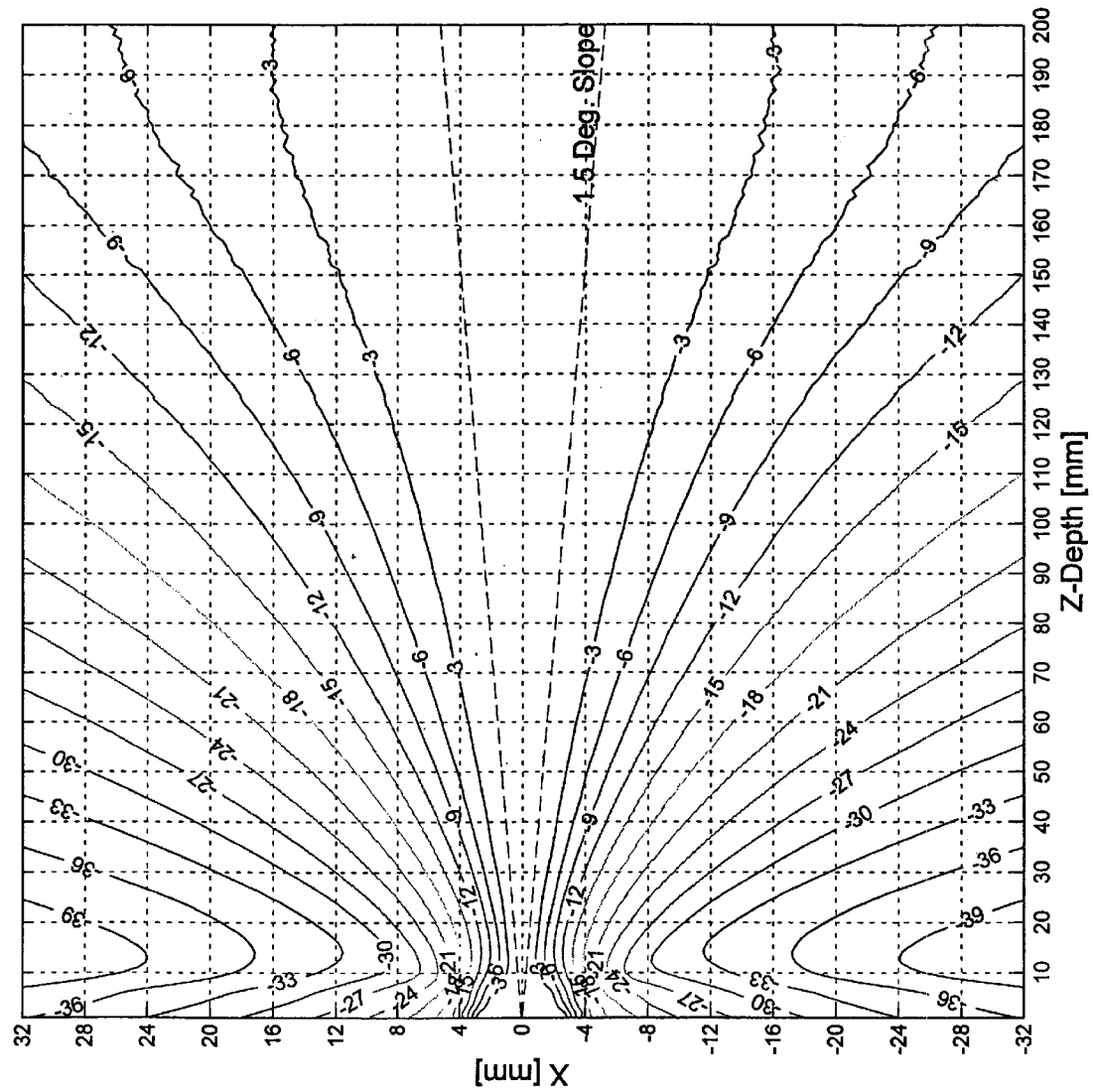
Figure 10A:
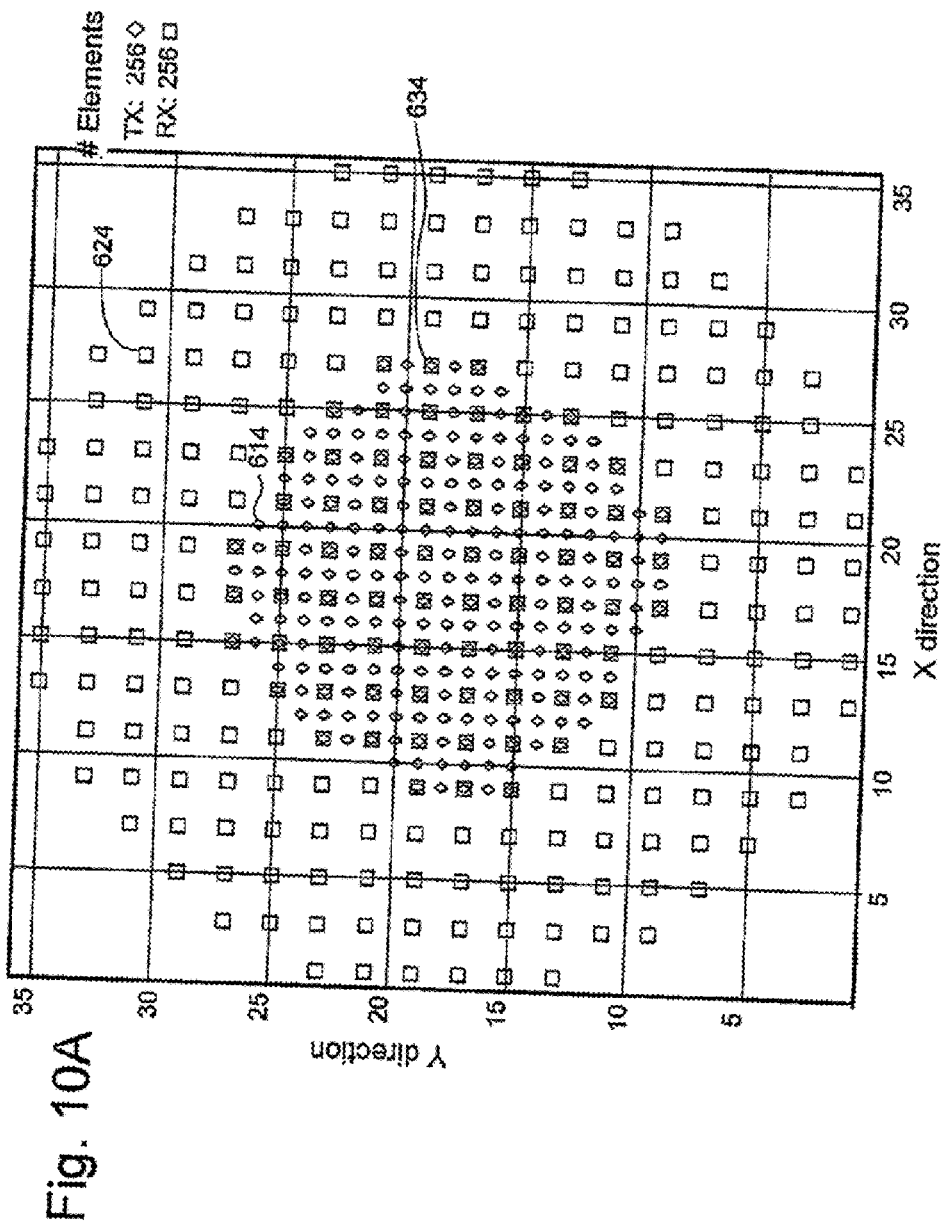
Figure 10B:
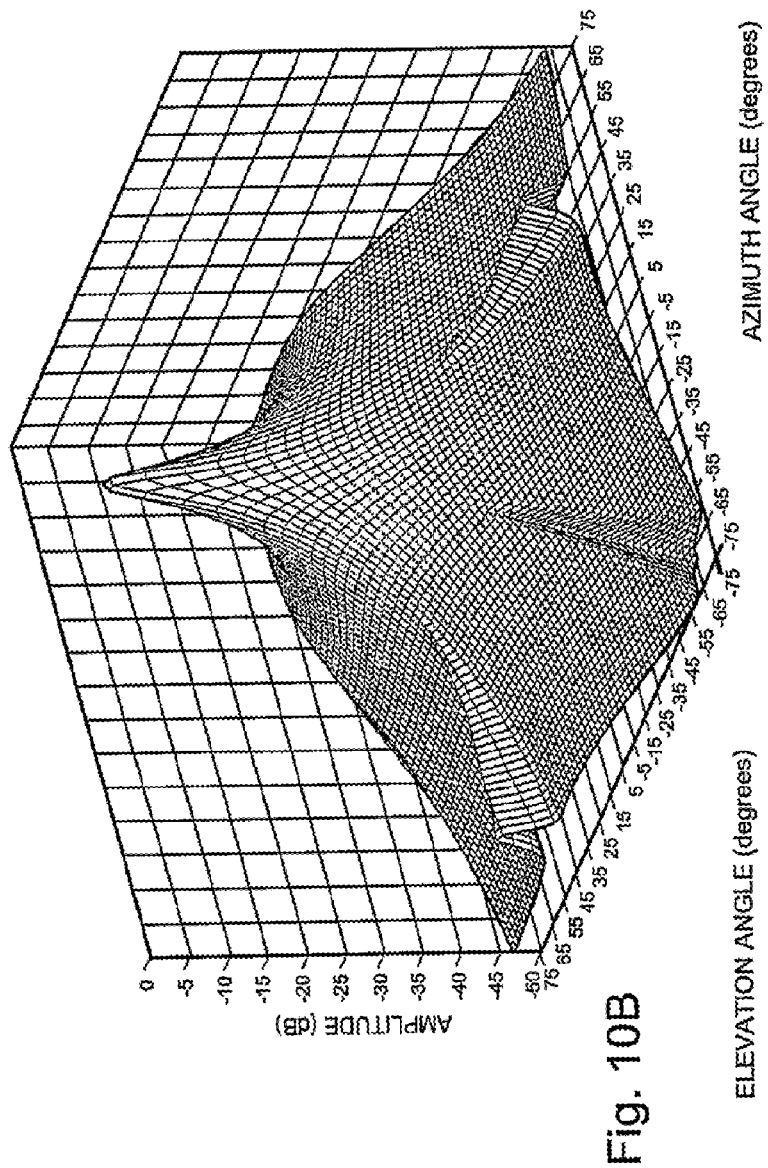
Figure 10C:
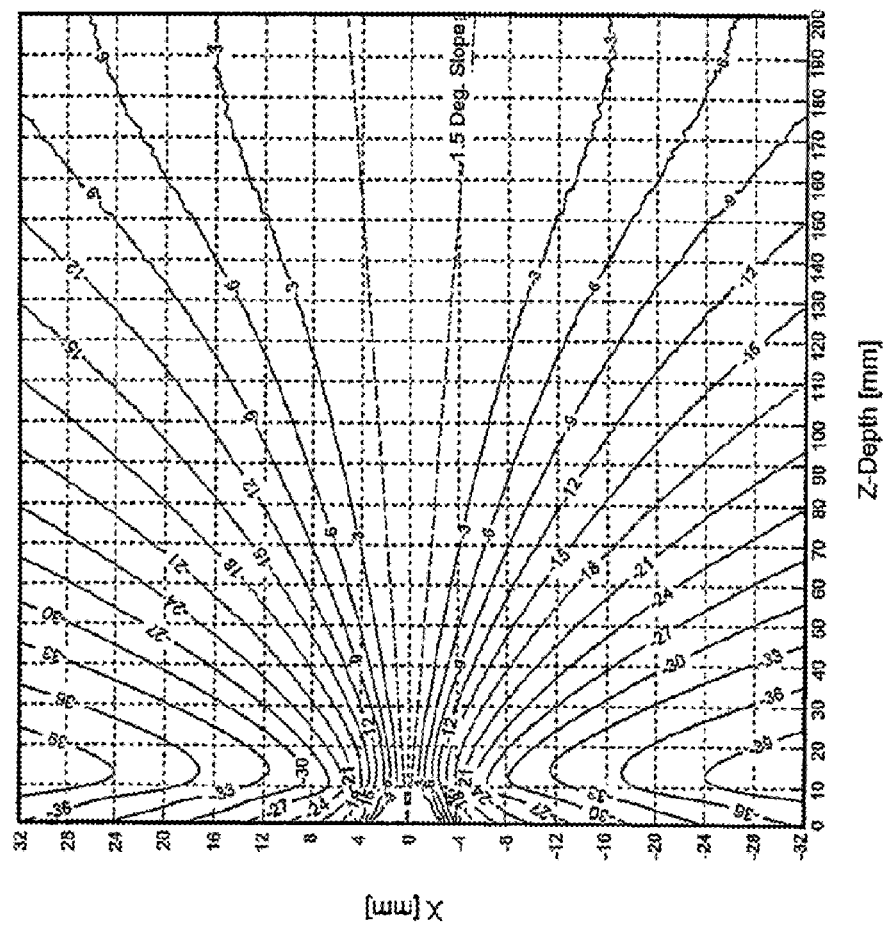
Figure 11A:
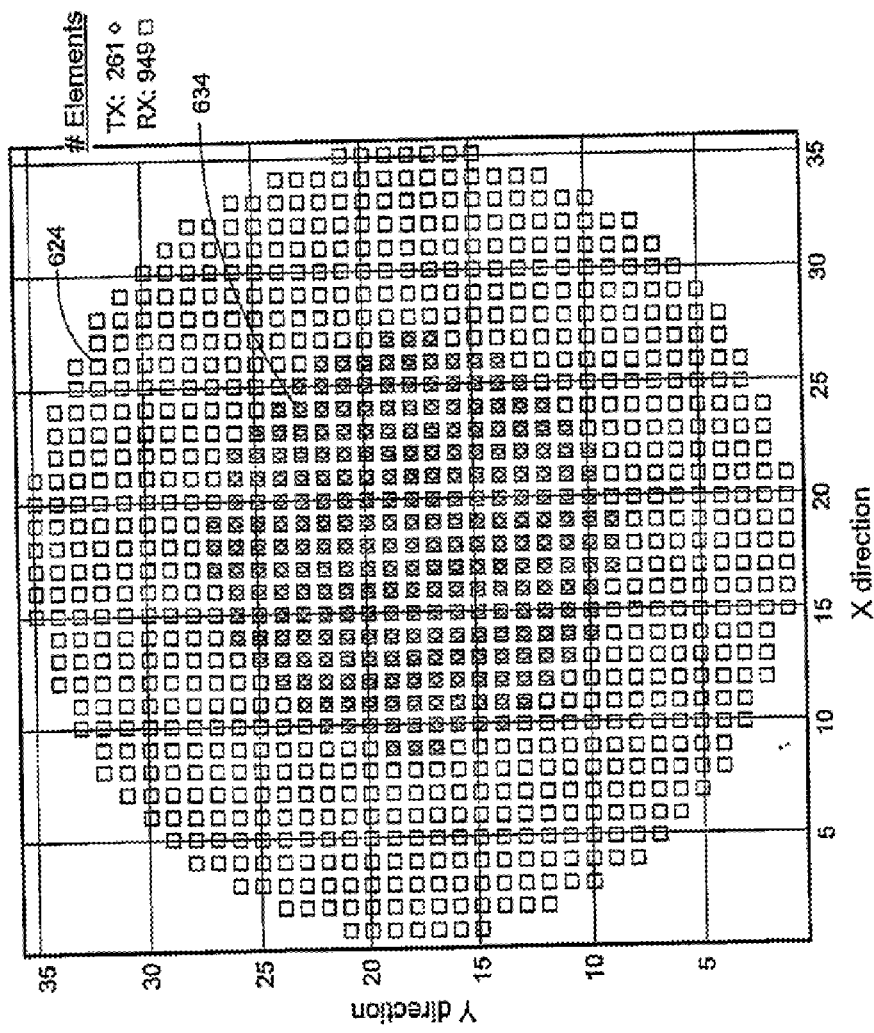

FIG. 10A shows an arrangement of elements with slightly more total elements than shown in FIG. 8A. FIG. 10A uses a sparse array of receive elements 624 and shared transmit/receive elements 634 and an inner octagon with a dense array of transmit elements 614 filling the gaps between the sparse array of shared transmit/receive elements 634.

While FIG. 10B is comparable to FIG. 8B, FIG. 10C has a much broader pattern than seen in either FIG. 8C or FIG. 9C. This pattern would be undesirable as it would complicate the ability to focus inquiry on a small zone several inches into a body.

Figure 11A:
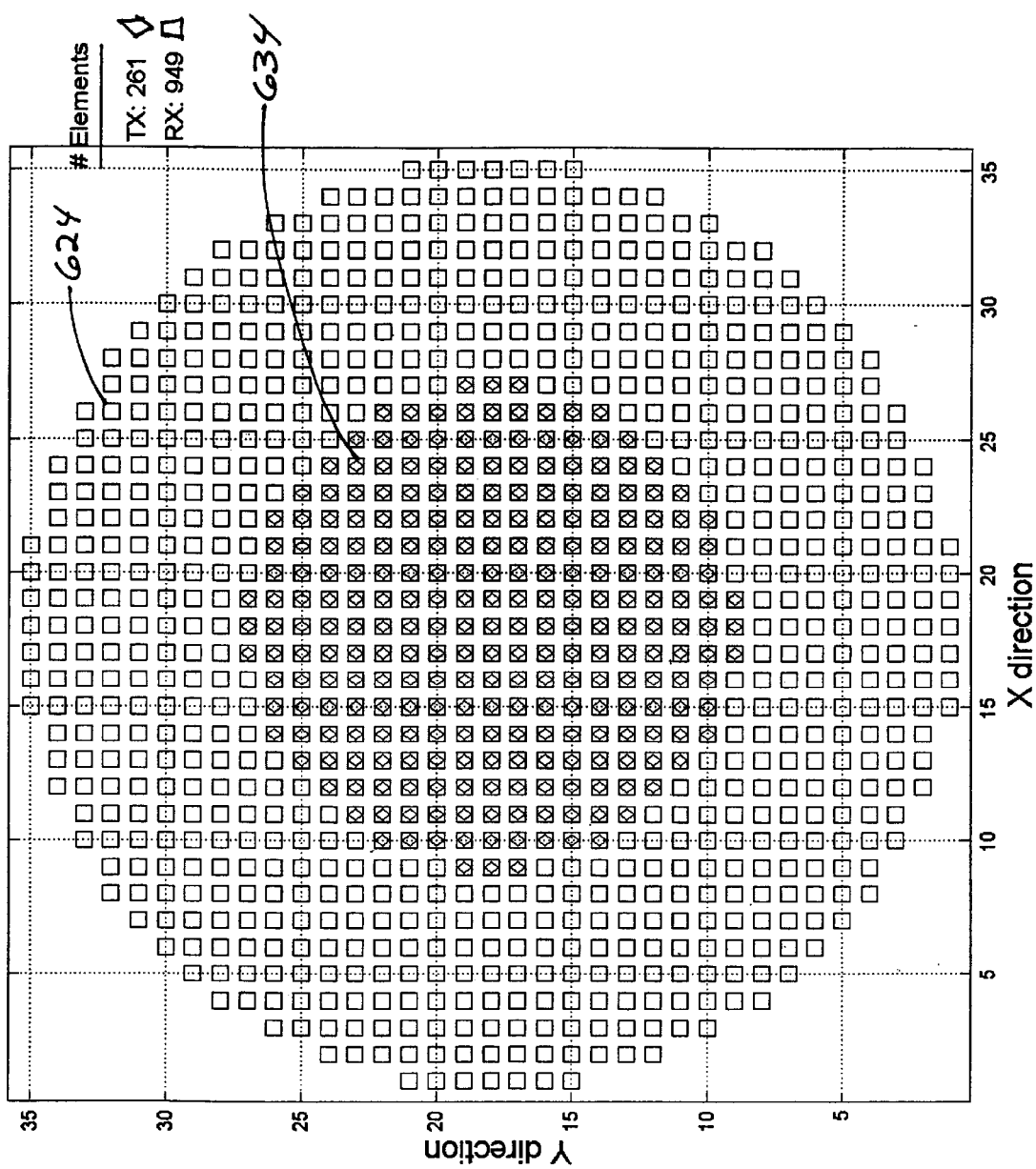
FIGS. 11A and 11B show another possible array with many receive elements and the simulated results from the beam pattern.
Figure 11B:
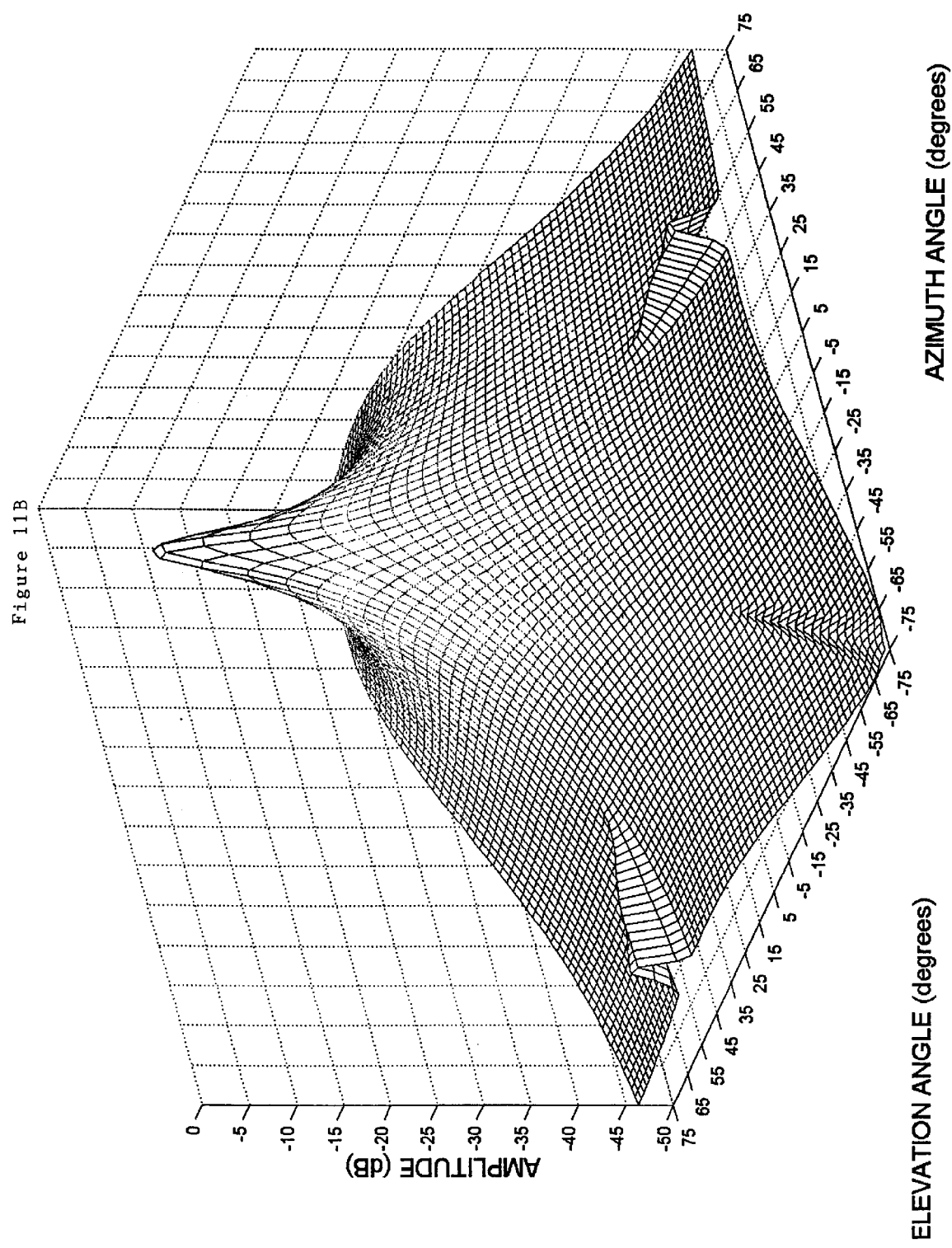
Figure 2:
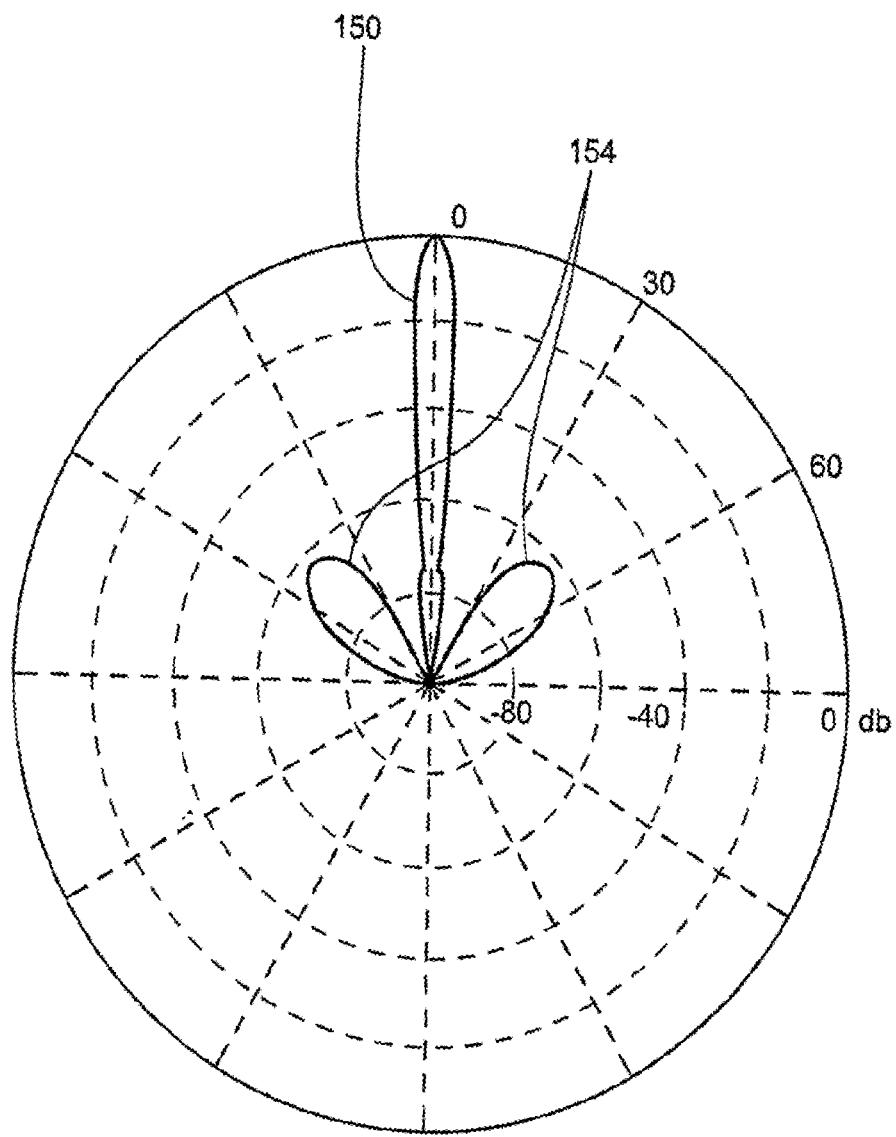
Figure 3:
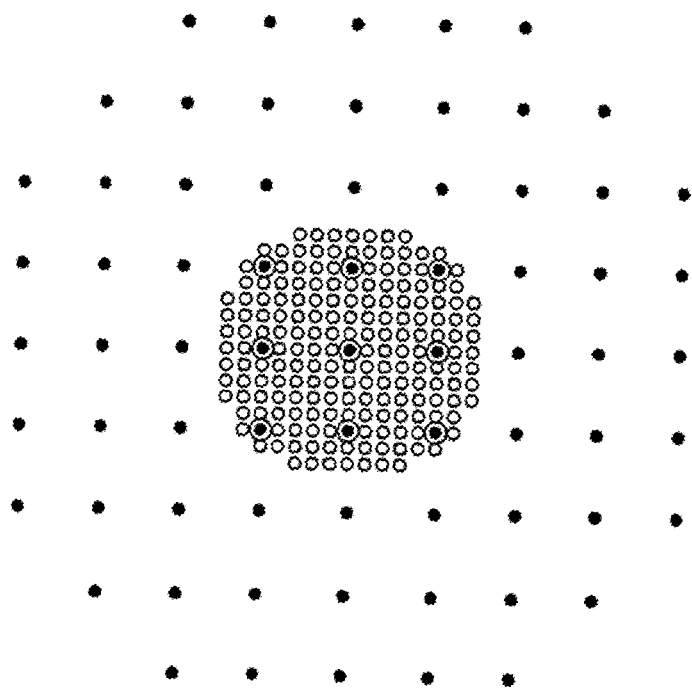

FIG. 11A shows a dense array of receive elements 624 with a center region having a dense array of shared transmit/receive elements 634. This is a very resource intensive array that uses a great number of total elements, including shared transmit/receive elements. Surprisingly, the results as shown in FIG. 11B are essentially comparable to the results shown in FIG. 8B.

The simulation results demonstrate that an array of the type suggested by this invention (FIG. 8A) produces results comparable with an array with many more elements (FIG. 11A) and much better than other sparse arrays (FIGS. 9A and 10A).

Alternative Embodiments

A) Use of Shared T/R Elements

Figure 6:
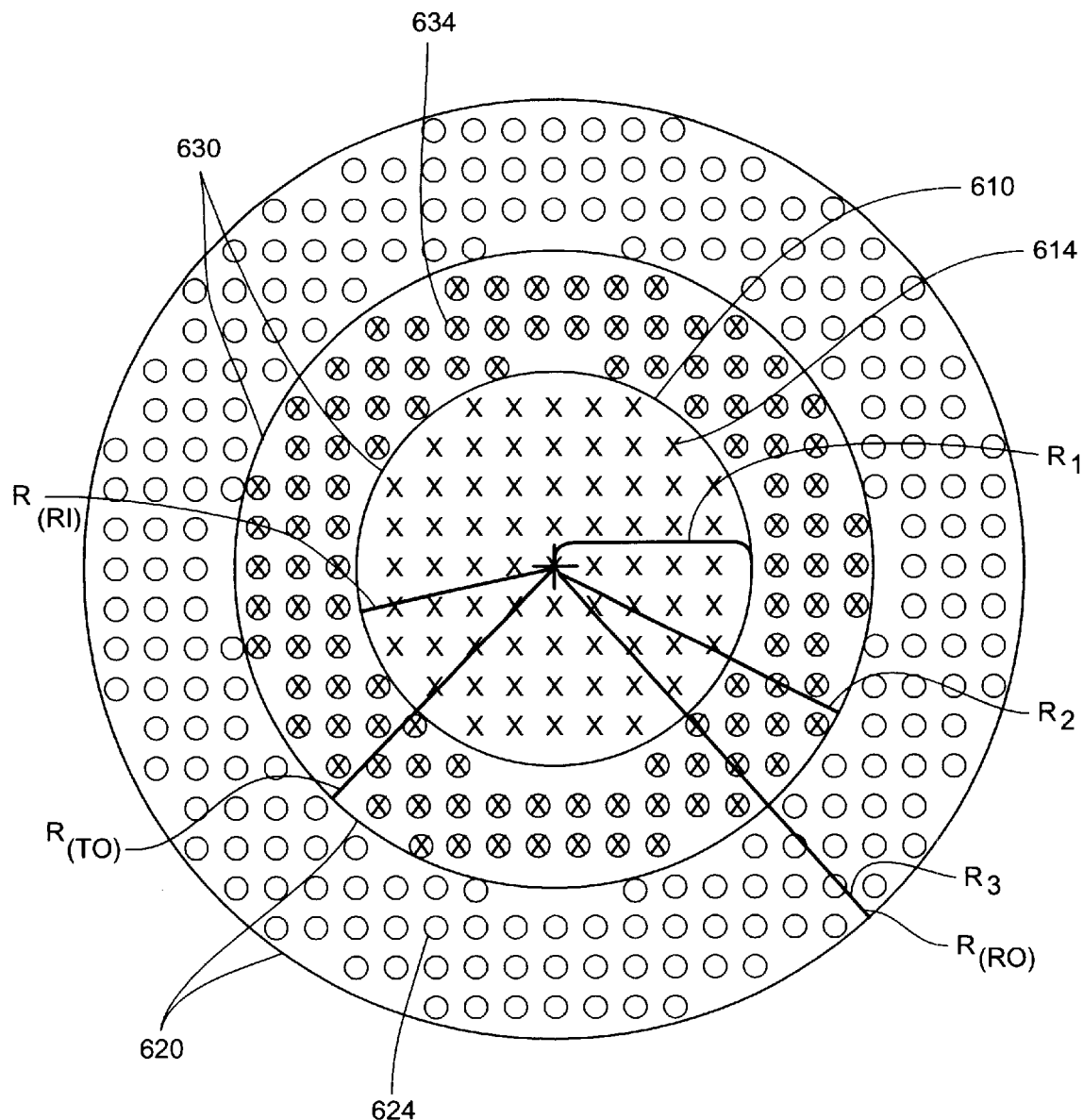
FIG. 6 illustrates an alternative embodiment with an intermediate zone using shared transmit/receive elements to augment the inner region of transmit elements and the outer region or receive elements.

In one alternative embodiment, an array 600 is comprised of a core and two annular rings. The inner core 610 of transmit elements 614 is contained in the region from the center to $R_1$. The inner core is surrounded by an annular region 620 of receive elements 624 in a region defined by center and radius measurements $R_2$ and $R_3$. In this embodiment, the annular region 630 defined by the center and $R_1$ to $R_2$ contains shared transmit/receive elements 634. As shown in FIG. 6, the shared transmit/receive elements fill this annular space but this is not a requirement for this embodiment.

Thus the region of transmit elements from the center to $R_{(TO)}$. $R_{(TO)}$ would be extended in this embodiment from $R_1$ to $R_2$.

The region of receive elements would be extended from the annular space defined by $R_2$ to $R_3$ to include the annular space from $R_1$ to $R_2$. Thus, $R_{(RI)}$ would be less than $R_{(TO)}$ and the receive and transmit arrays would overlap.

The use of shared T/R elements has been illustrated with concentric circles but can be incorporated into a design using concentric polygons.

Figure 7:
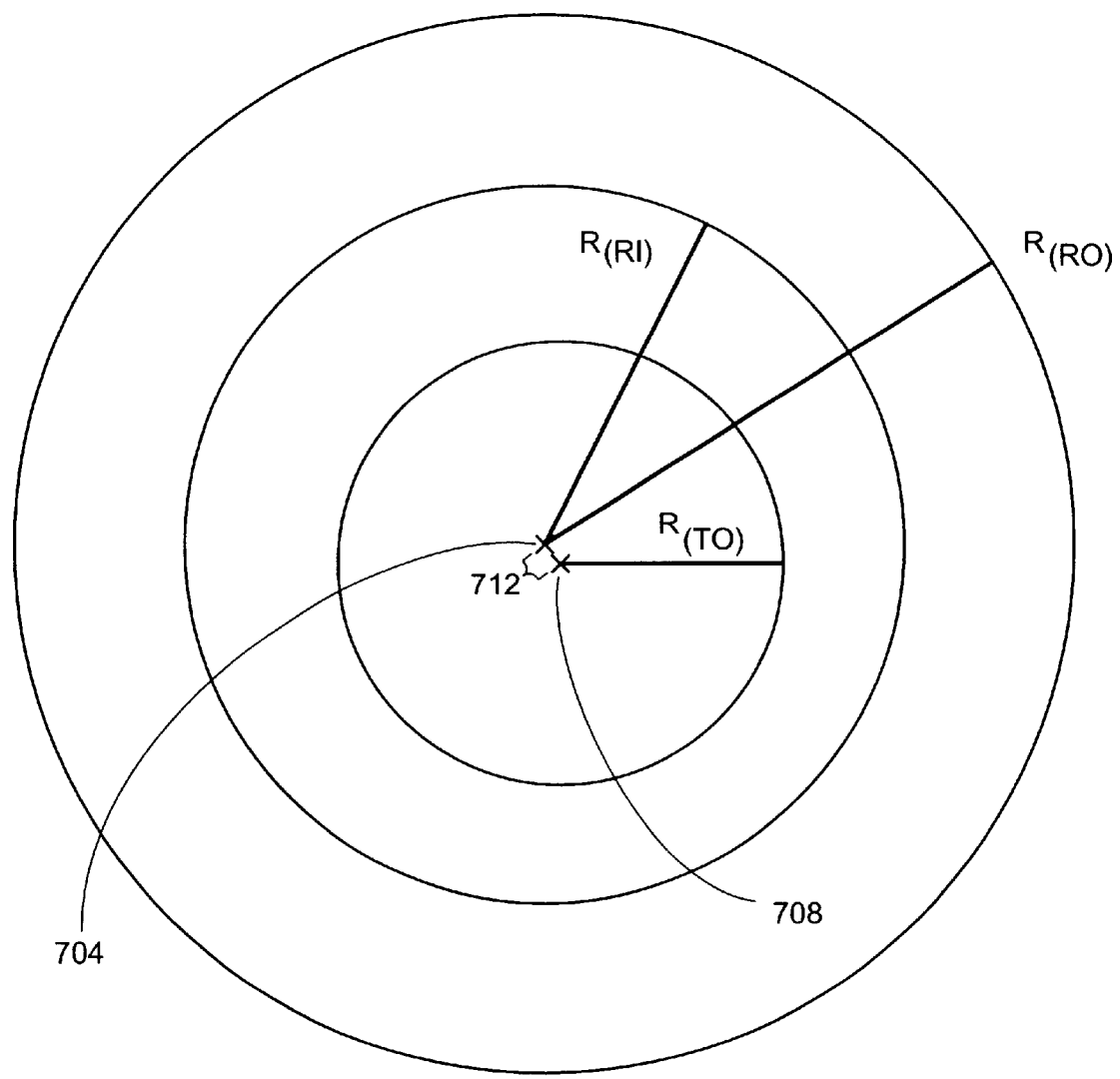
FIG. 7 illustrates an alternative embodiment that has a center of the transmit array that is not identical to the center for the receive array.

FIG. 7 illustrates another embodiment of the present invention. In this embodiment, the center 704 used for defining the area of the transmit array differs from the center 708 used for defining the receive array. As indicated in FIG. 7, the distance delta 712 is the distance between the center 704 for the transmit array and the center 708 for the annular receive array.

The difference delta 712 is sufficiently small so that the transmit array does not overlap with the receive array. Thus $R_{(TO)}$ plus distance delta 712 is less than $R_{(RI)}$.

This embodiment has been illustrated with circles and annular spaces but could be extended to polygons and annular polygons.

B) Single Ring of Shared T/R Elements

A single ring of shared T/R elements could be used, especially in a device that was not going to use parallel processing of received signals. By having a ring with a relatively large diameter, the array would produce a high-resolution image. Parallel processing would be difficult with such a device. One reason that it would be difficult to use such a device for parallel processing is the complexity of interleaving the various receive activities with the transmit function for shared transmit/receive elements.

C) Irregular Patterns within the Receive or Transmit Arrays

Although the preferred embodiments of the present invention teach the use of transmit and receive arrays with sets of elements arranged without gaps or other irregularities, many of the advantages of the present invention could be attained with arrays having some level of irregularity. For example, the outer annular space or annular polygon could have one or more gaps in the array of receive elements. It is likely that these gaps would lead to a degraded image, but this may be acceptable in some situations.

Those skilled in the art will recognize that the methods and apparatus of the present invention have many applications including both 2D and 3D volumetric scanning and that the present invention is not limited to the specific examples given to promote understanding of the present invention. For, example, implementations may use multiple transmit and or receive rings within the scope of the teachings of this patent.

Moreover, the scope of the present invention covers the range of variations, modifications, and substitutes for the system components described herein, as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

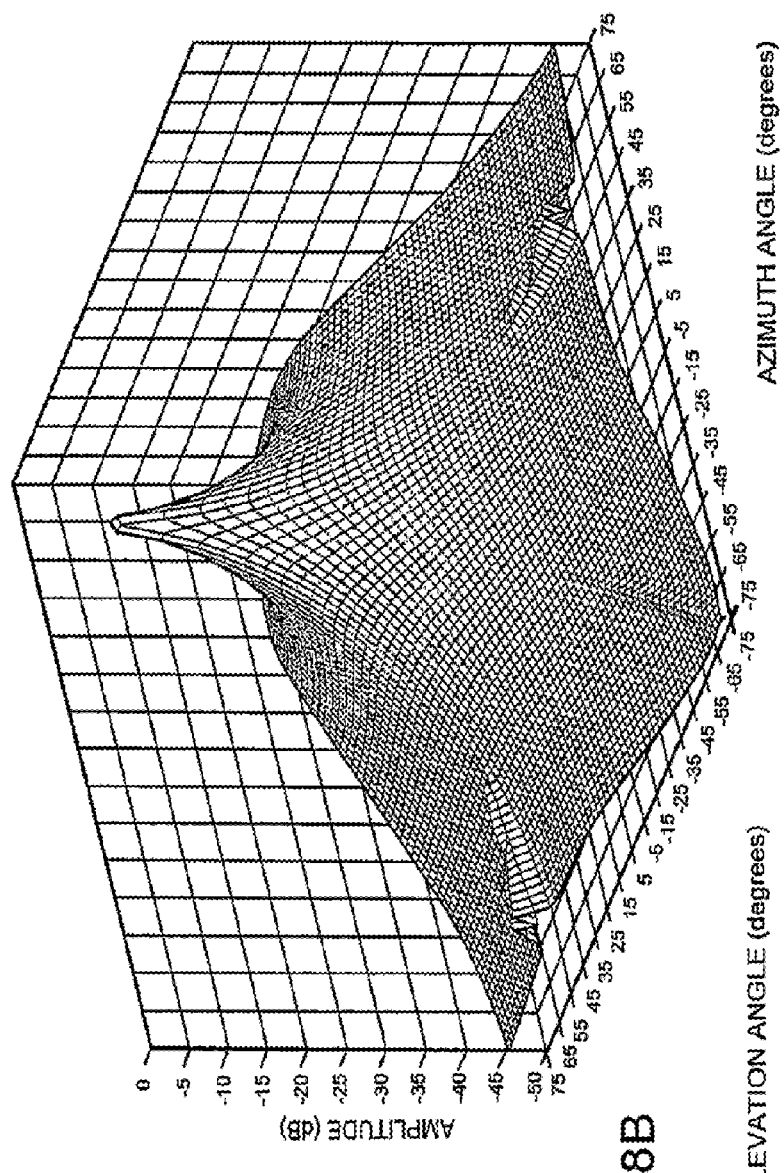

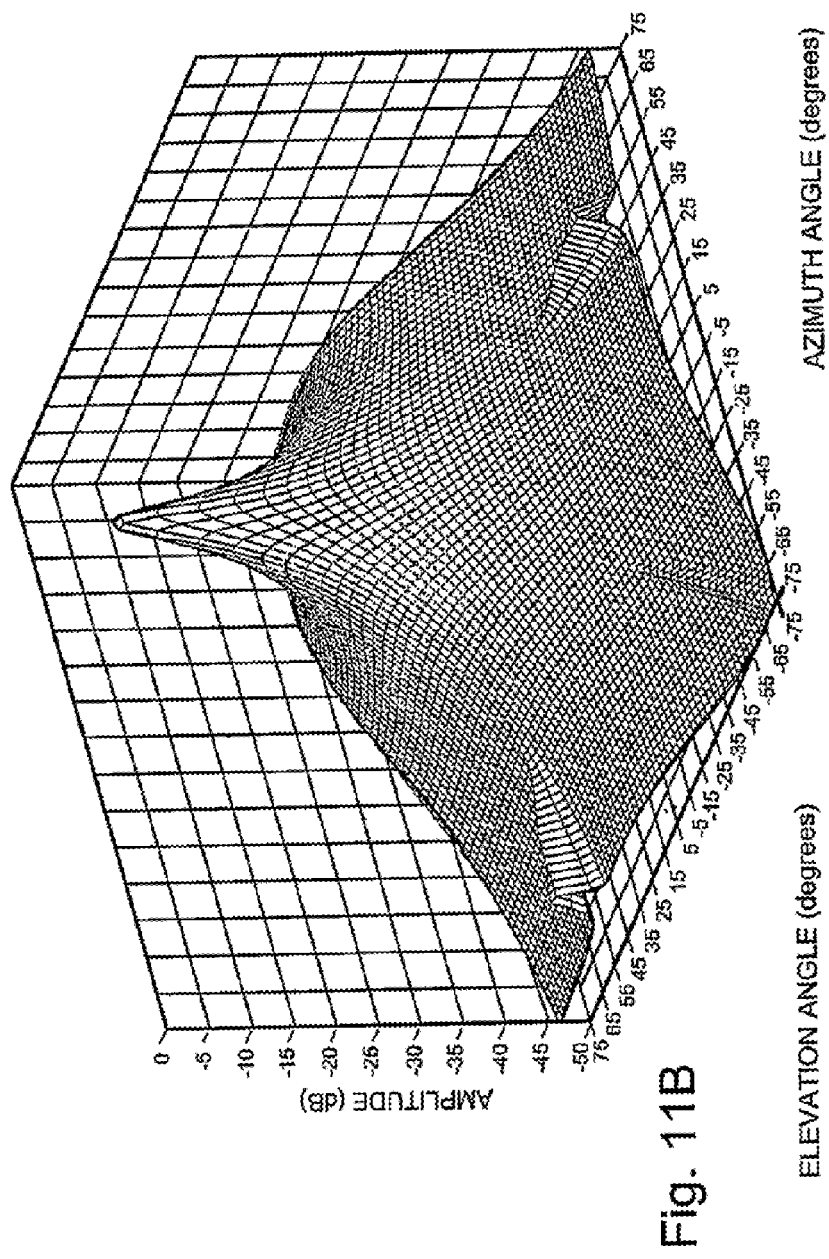

What is claimed is:

1. An array structure for transmitting and receiving energy having a center axis, comprising:

a transmit array comprising elements spaced at intervals equal to one half of the wavelength of an operating frequency within a bandwidth of the transmit elements, a centerline of the transmit array being substantially coaxial with the center axis, an area containing the transmit array defined by a space within an annular space between radius R(T inner) and radius R(T outer) taken with respect to the enter axis; and a separate receive array comprising receive elements spaced at intervals equal to one half of the wavelength of an operating frequency within a bandwidth of the transmit elements, a centerline of the transmit array substantially coaxial with the center axis, an area of the receive array defined by the space within the annular space between radius R(R inner) and radius R(R outer) taken with respect to the center axis where R(T outer) is greater than R(T inner), R(R inner) is greater than R(T outer) and R(R outer is greater than R(R inner) such that the receive array is within an annular region outside of the area containing the transmit array.

2. The array structure of claim 1 wherein R(T inner) is zero such that the area containing the transmit array is defined by a circular space within radius R(T outer).

3. The array structure of claim 1 wherein: the transmit elements have a typical interelement spacing in an azimuth direction and a typical interelement spacing in an elevation direction to form a spacing grid; and the transmit array has at least one gap in the spacing grid where there is a gap between adjacent connected transmit elements that is at least approximately twice the interelement spacing in the azimuth direction and there is a gap between adjacent connected transmit elements that is at least approximately twice the interelement spacing in the elevation direction.

4. The array structure of claim 1 wherein the transmit array is surrounded by a dead band region lacking either connected transmit elements or connected receive elements, the dead band region contained in an annular area around center axis defined by R(DB inner) and R(DB outer) where R(DB inner) is not less than R(T outer) and R(DB outer) is not greater than R(R inner).

5. The array structure of claim 1 wherein the transmit array is surrounded by a TR region comprised of elements that are used as transmit elements and as receive elements, the TR region contained in the annular area around center axis defined by R(TR inner) and R(TR outer) where R(TR inner) is not less than R(T outer) and R(TR outer) is not greater than R(R inner).

6. The array of claim 1 wherein for a given mode of operation, none of the active receive elements are used as transmit elements and none of the active transmit elements are used as receive elements.

7. The array of claim 1 wherein the transmit elements are designed to have a resonant frequency of f and the receive elements are designed to have a resonant frequency of other than f.

8. The array of claim 7 wherein the transmit elements are designed to have the resonant frequency of f and the receive elements are designed to have a resonant frequency of approximately a harmonic of f.

9. The array of claim 7 wherein the transmit elements are designed to have the resonant frequency of f and the receive elements are designed to have a resonant frequency of approximately a sub-harmonic of f.

10. The array of claim 7 wherein the transmit elements are designed to have the resonant frequency of f and the receive elements are designed to have a resonant frequency of approximately a fractional harmonic of f.

11. The array of claim 1 wherein:

the transmit and receive elements are located in a scanning head;

the scanning head is connected by a cable to a scanning device;

the scanning head contains a set of pre-amps for the receive elements, the pre-amps operating to produce a first voltage;

the scanning head contains a set of transmitters for the transmit elements operating at a second voltage; and the second voltage is at least an order of magnitude greater than the first voltage.

12. An array structure for transmitting and receiving energy having a center axis, comprising:
- a transmit array comprising transmit elements spaced at intervals equal to one half of the wavelength of an operating frequency within a bandwidth of the transmit elements, the center of the transmit array being substantially coaxial with the center axis, an area of the transmit array defined by a space within a polygon defined by a set of n vertices located at approximately distance V(To) from the center axis; an
- a separate receive array comprising receive elements spaced at intervals equal to one half of the wavelength of an operating frequency within a bandwidth of the receive elements, a region containing the receive array defined by an annular polygonal space defined by an inner polygon and an outer polygon wherein:
  - the inner polygon is defined by a set of nn vertices located at approximately distance V(Ri) from the center axis;
  - the outer polygon is defined by a set of nnn vertices located at approximately distance V(Ro) from the center axis;
  - V(To) is less than V(Ri); and
  - V(Ri) is less than V(Ro).

13. The array structure of claim 12 wherein:
the transmit elements have a typical interelement spacing in an azimuth direction and a typical interelement spacing in an elevation direction to form a spacing grid; and the transmit array has at least one gap in the spacing grid where there is a gap between adjacent connected transmit elements that is at least approximately twice the typical interelement spacing in the azimuth direction and there is a gap between adjacent connected transmit elements that is at least approximately twice the typical interelement spacing in the elevation direction.

14. The array structure of claim 12 wherein:
the transmit array is surrounded by a dead band region lacking either connected transmit elements or connected receive elements, the dead band region contained in an annular polygonal space defined by an inner polygon and an outer polygon wherein:
  - the inner polygon is defined by a set of n vertices located at approximately distance V(To) from the center axis; and
  - the outer polygon is defined by a set of nn vertices located at approximately distance V(Ri).

15. The array structure of claim 12 wherein:
the transmit array is surrounded by TR region comprised of elements that are used as transmit elements and as receive elements, the TR region contained in the annular polygonal space defined by an inner polygon and an outer polygon wherein:
  - the inner polygon is defined by a set of m vertices located at approximately distance V(TR inner);
  - the outer polygon is defined by a set of mm vertices located at approximately distance V(TR outer);
  - V(TR inner) is greater than V(To); and
  - V(TR outer) is less than V(Ri).

16. The array of claim 12 wherein none of the receive elements for a particular scanning function are used during the same scanning function as transmit elements and none of the transmit elements for that particular scanning function are used during that same scanning function as receive elements.

17. The array of claim 12 wherein the transmit elements are designed to have a resonant frequency of f and, the receive elements are designed to have a resonant frequency other than f.

18. The array of claim 17 wherein the transmit elements are designed to have the resonant frequency of f and, the receive elements are designed to have a resonant frequency of approximately a harmonic of f.

19. The array of claim 17 wherein the transmit elements are designed to have the resonant frequency of f and the receive elements are designed to have a resonant frequency of approximately a sub-harmonic of f.

20. The array of claim 17 wherein the transmit elements are designed to have the resonant frequency of f and the receive elements are designed to have a resonant frequency of approximately a fractional harmonic of f.

21. The array of claim 12 wherein:
- the transmit and the receive elements are located in a scanning head;
- the scanning head is connected by a cable to a scanning device;
- the scanning head contains a set of pre-amps for the receive elements operating at a first voltage;
- the scanning head contains a set of transmitters for the transmit elements operating at a second voltage; and
- the second voltage is at least an order of magnitude greater than the first voltage.

22. A method of acquiring information for medical imaging comprising:
- transmitting energy from an inner array of transmit elements spaced at intervals equal to one half of the wavelength of an operating frequency within a bandwidth of the transmit elements to electronically illuminate a target area within a body; then
- using a separate set of receive elements located in a band of receive elements spaced at intervals equal to one half of the wavelength of an operating frequency within a bandwidth of the receive elements, the band located outside the inner array of transmit elements, the set of receive elements used to receive reflected energy from a fraction of the illuminated target area; and
- using parallel processing to combine information from reflected energy from several sets of data collected by various sets of receive elements to form a three-dimensional image of the target area within the body.

23. The method of claim 22 wherein:
- the transmit elements are optimized to operate at a transmit frequency;
- the receive elements are optimized to operate at a receive frequency which is different than the transmit frequency; and
- the information for medical imaging is acquired using harmonic imaging techniques.

* * * * *

UNITED STATES PATENT AND TRADEMARK OFFICE
CERTIFICATE OF CORRECTION

PATENT NO. : 6,783,497 B2
APPLICATION NO. : 10/154149
DATED : August 31, 2004
INVENTOR(S) : Grenon et al.

It is certified that error appears in the above-identified patent and that said Letters Patent is hereby corrected as shown below:

Column 11, Line 63, replace the word "enter" before axis with the word --center--

Column 11, Line 67, replace the word "transmit" before elements with the word --receive--

Column 11, Line 67, replace the word "transmit" before array with the word --receive--

Column 13, Line 10, replace the word "an" after axis; with the word --and--

Figure 1:
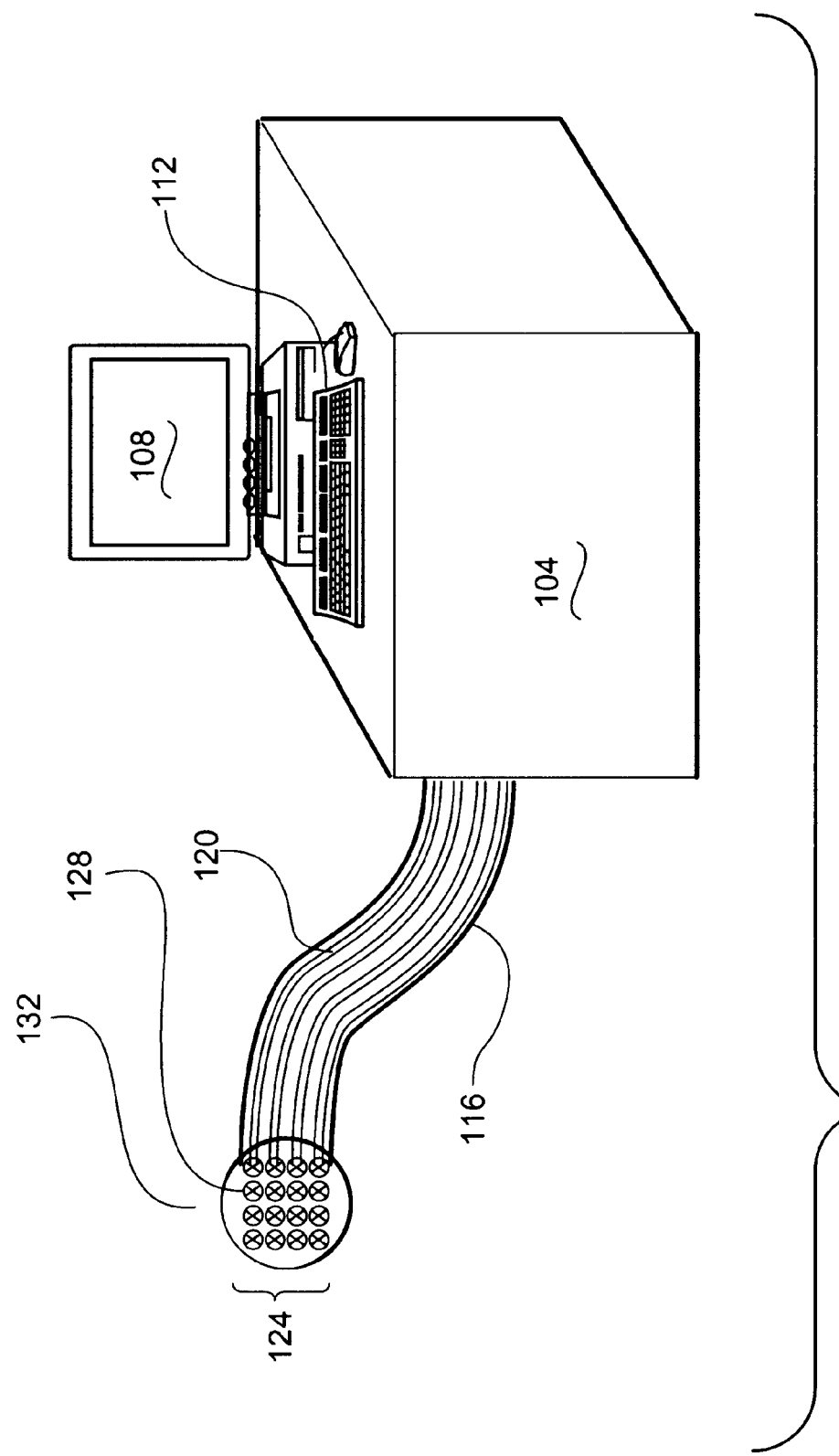
FIG. 1 shows the environment for the present invention, more specifically, the relevant components in a medical imaging device.
Figure 2:
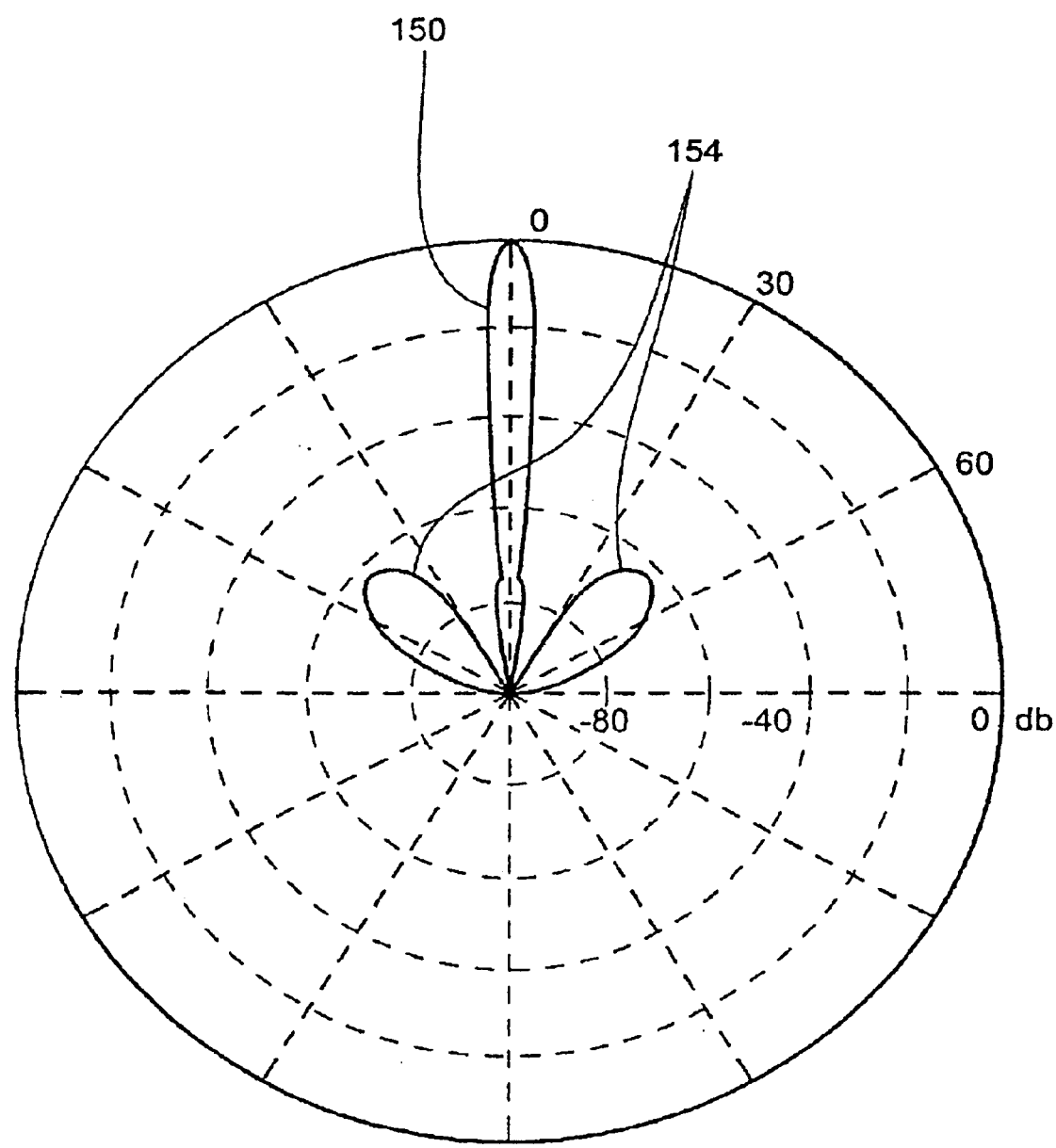
FIG. 2 illustrates the prior art concepts of a main lobe and secondary lobes.
Figure 3:
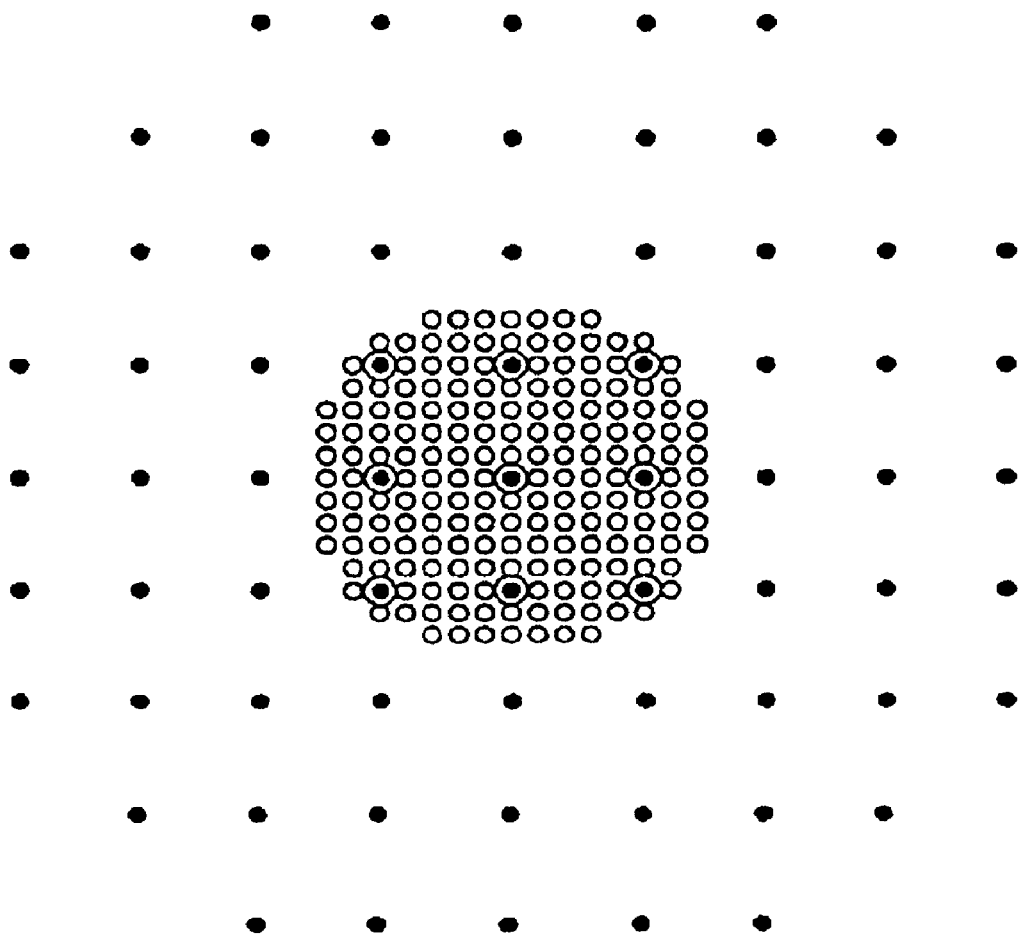
FIG. 3 illustrates one prior art solution of a sparse array designed for use with apodization.

Replace informal Figure 2 with revised Figure 2
Replace informal Figure 3 with revised Figure 3

Replace informal Figure 8A with revised Figure 8A
Replace informal Figure 8B with revised Figure 8B
Replace informal Figure 8C with revised Figure 8C Replace informal Figure 9A with revised Figure 9A
Replace informal Figure 9B with revised Figure 9B
Replace informal Figure 9C with revised Figure 9C Replace informal Figure 10A with revised Figure 10A
Replace informal Figure 10B with revised Figure 10B
Replace informal Figure 10C with revised Figure 10C

UNITED STATES PATENT AND TRADEMARK OFFICE
CERTIFICATE OF CORRECTION

PATENT NO. : 6,783,497 B2
APPLICATION NO. : 10/154149
DATED : August 31, 2004
INVENTOR(S) : Grenon et al.

It is certified that error appears in the above-identified patent and that said Letters Patent is hereby corrected as shown below:

Replace informal Figure 11A with revised Figure 11A
Replace informal Figure 11B with revised Figure 11B Signed and Sealed this Ninth Day of January, 2007

JON W. DUDAS
*Director of the United States Patent and Trademark Office*

- ⊙ transmit and receive
- • receive only
- ○ transmit only